(12) United States Patent
Kuboi et al.

(10) Patent No.: US 10,821,260 B2
(45) Date of Patent: Nov. 3, 2020

(54) STATE CONTROL APPARATUS, STATE CONTROL METHOD, AND STATE CONTROL SYSTEM

(71) Applicant: Sony Corporation, Tokyo (JP)

(72) Inventors: Nobuyuki Kuboi, Kanagawa (JP); Takashi Kinoshita, Kanagawa (JP); Shinya Yamakawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 909 days.

(21) Appl. No.: 15/510,465

(22) PCT Filed: Jul. 16, 2015

(86) PCT No.: PCT/JP2015/070424
§ 371 (c)(1),
(2) Date: Mar. 10, 2017

(87) PCT Pub. No.: WO2016/042908
PCT Pub. Date: Mar. 24, 2016

(65) Prior Publication Data
US 2017/0304581 A1    Oct. 26, 2017

(30) Foreign Application Priority Data

Sep. 19, 2014 (JP) .................................. 2014-190823

(51) Int. Cl.
*A61M 21/00* (2006.01)
*G06F 16/435* (2019.01)
(Continued)

(52) U.S. Cl.
CPC ......... *A61M 21/00* (2013.01); *A61B 5/14507* (2013.01); *A61B 5/14546* (2013.01);
(Continued)

(58) Field of Classification Search
CPC .................. A61M 21/00; A61M 21/02; A61M 2021/0005; A61M 2021/0011;
(Continued)

(56) References Cited

U.S. PATENT DOCUMENTS

2003/0225095 A1* 12/2003 McCulloch .......... A61B 5/4815
514/249
2004/0263337 A1    12/2004 Terauchi et al.
(Continued)

FOREIGN PATENT DOCUMENTS

JP    2001-252265 A    9/2001
JP    2005-021255 A    1/2005
(Continued)

OTHER PUBLICATIONS

International Search Report and Written Opinion and English translation thereof dated Aug. 11, 2015 in connection with International Application No. PCT/JP2015/070424.
(Continued)

Primary Examiner — Carrie R Dorna
(74) Attorney, Agent, or Firm — Wolf, Greenfield & Sacks, P.C.

(57) ABSTRACT

A state control apparatus including: an acquiring unit configured to acquire a state index indicating a state of target feeling based on biological information corresponding to the target feeling which is feeling of a target to be guided, the biological information being detected from a guide target whose state of feeling is to be guided; and a state control unit configured to determine a feeling guiding medium to be used for guiding the state of the target feeling based on the acquired state index and pattern information which is associated with the feeling guiding medium for guiding the state of the target feeling and which indicates a pattern of temporal change of the state index so that the state of the target
(Continued)

feeling becomes a predetermined set state, and control the state of the target feeling of the guide target by performing processing relating to the determined feeling guiding medium. The biological information includes information indicating a detection result of an enzyme.

17 Claims, 26 Drawing Sheets

(51) Int. Cl.
    *A61B 5/145*     (2006.01)
    *G06F 16/2457*     (2019.01)
    *G06F 16/00*     (2019.01)

(52) U.S. Cl.
    CPC ........ *G06F 16/00* (2019.01); *G06F 16/24575* (2019.01); *G06F 16/436* (2019.01); *A61M 2021/0022* (2013.01); *A61M 2205/3553* (2013.01); *A61M 2210/0625* (2013.01); *A61M 2230/005* (2013.01); *A61M 2230/06* (2013.01)

(58) Field of Classification Search
    CPC .. A61M 2021/0016; A61M 2021/0022; A61M 2021/0027; A61M 2021/0044; A61M 2021/005; A61M 2021/0083; A61M 2021/0088; A61B 5/14546; A61B 5/1486
    See application file for complete search history.

(56) References Cited

U.S. PATENT DOCUMENTS

| | | | | |
|---|---|---|---|---|
| 2005/0075532 A1* | 4/2005 | Lee | ........................ | A61M 21/00 600/27 |
| 2011/0270053 A1* | 11/2011 | Utley | ..................... | A61B 5/082 600/309 |
| 2014/0277292 A1* | 9/2014 | Steel | .................... | A61N 5/0622 607/88 |

FOREIGN PATENT DOCUMENTS

| | | |
|---|---|---|
| JP | 2006-320621 A | 11/2006 |
| JP | 2010-266748 A | 11/2010 |

OTHER PUBLICATIONS

International Preliminary Report on Patentability and English translation thereof dated Mar. 30, 2017 in connection with International Application No. PCT/JP2015/070424.

\* cited by examiner

| CONTENT ID | GENRE | NAME OF SONG | SONG-WRITER | TIME-SERIES PATTERN OF S | VALUE OF S UPON REPRODUCTION | CORRELATION COEFFICIENT UPON REPRODUCTION | CUMULATIVE NUMBER OF TIMES OF REPRODUCTION |
|---|---|---|---|---|---|---|---|
| 001 | POPS | ○○ | AAA | ⌒ | 25 | 0.83 | 21 |
| 002 | JAZZ | ○△ | ABC | ⌇ | 63 | 0.45 | 5 |
| 003 | CLASSIC | □× | CCB | ⌒ | 101 | 0.92 | 32 |
| ... | ... | ... | ... | ... | ... | ... | ... |

B

| CONTENT ID | GENRE | NAME OF SONG | SONG-WRITER | TEMPO | S TIME-SERIES | VALUE OF S UPON REPRODUCTION | CORRELATION COEFFICIENT UPON REPRODUCTION | CUMULATIVE NUMBER OF TIMES OF REPRODUCTION | REPRODUCTION DATE AND TIME | REPRODUCTION TIME | REPRODUCTION LOCATION |
|---|---|---|---|---|---|---|---|---|---|---|---|
| 001 | POPS | ○○ | AAA | 150bpm | ⌒ | 25 | 0.83 | 21 | 2014/1/1 | AM 12:00 | MOUNTAIN |
| 002 | JAZZ | ○△ | ABC | 103bpm | ⌇ | 63 | 0.45 | 5 | 2013/12/25 | PM 21:00 | STORE |
| 003 | CLASSIC | □× | CCB | 62bpm | ⌒ | 101 | 0.92 | 32 | 2013/7/7 | PM 22:00 | SEA |
| ... | ... | ... | ... | ... | ... | ... | ... | ... | ... | ... | ... |

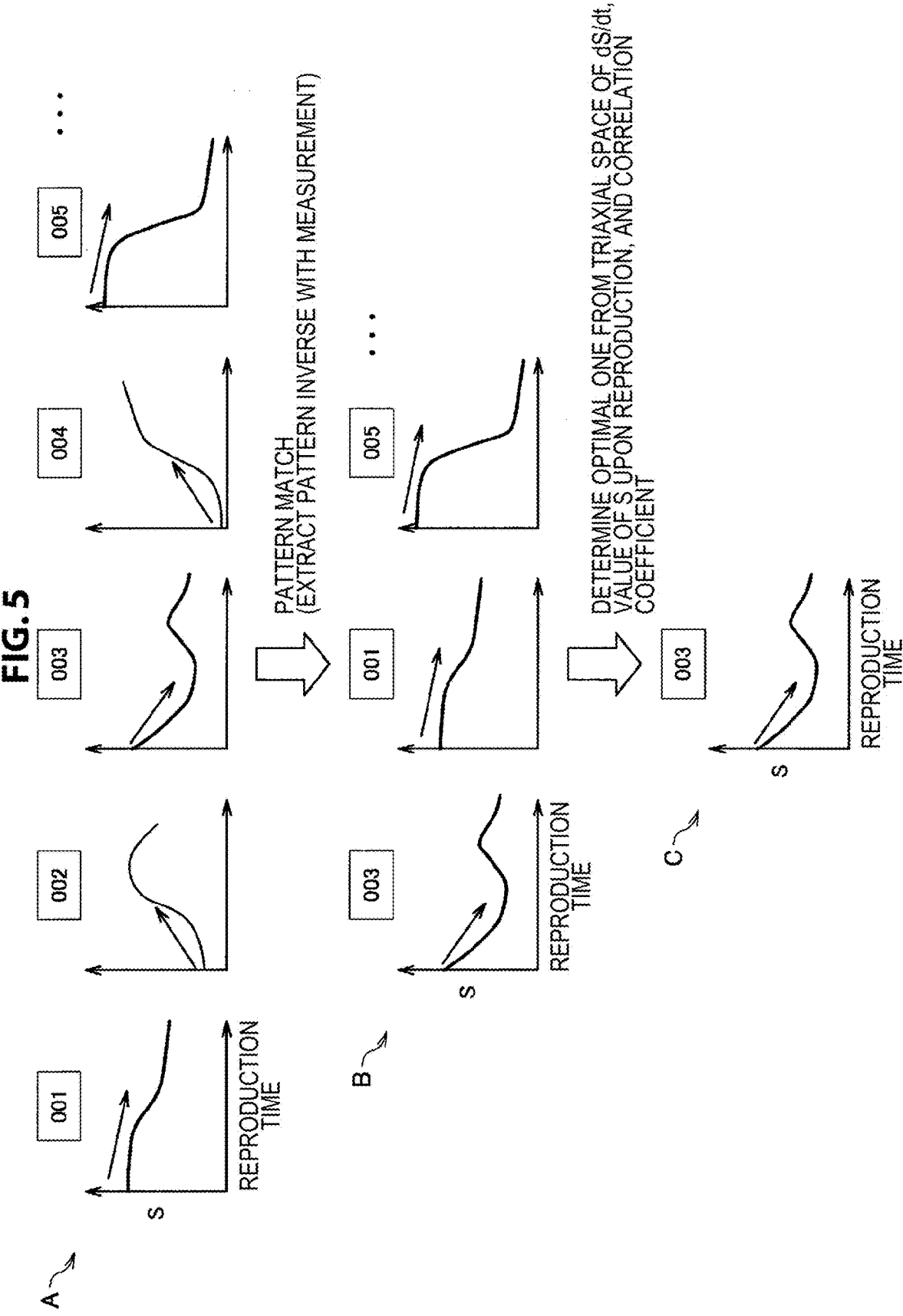

FIG. 11
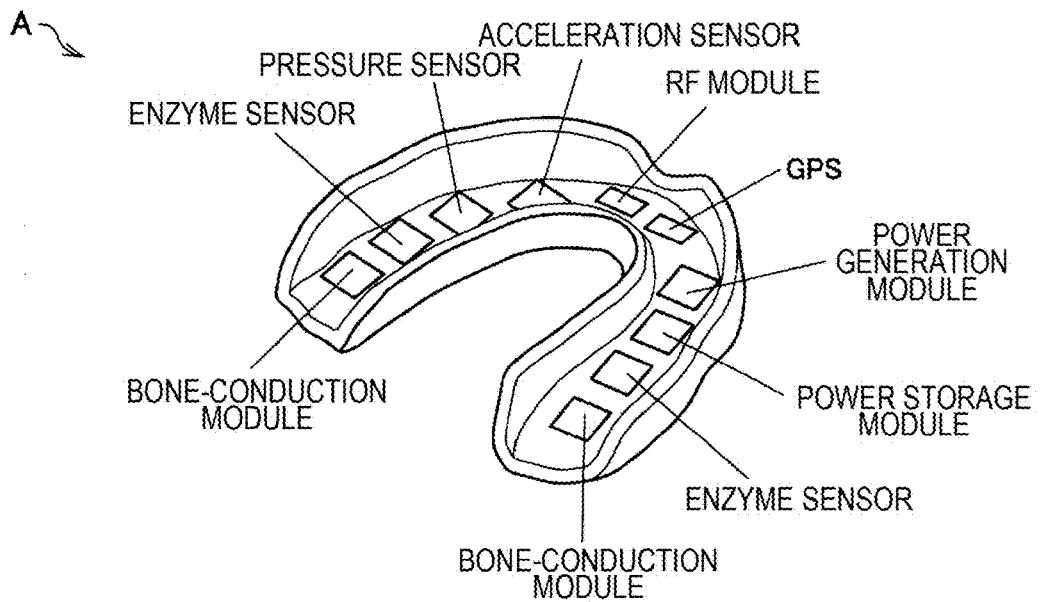
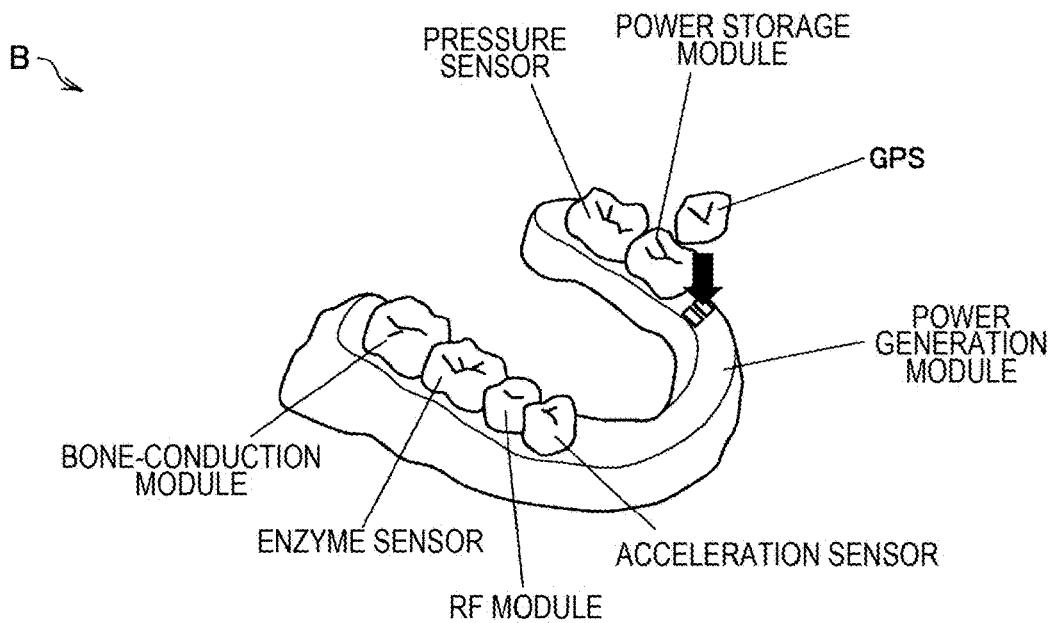
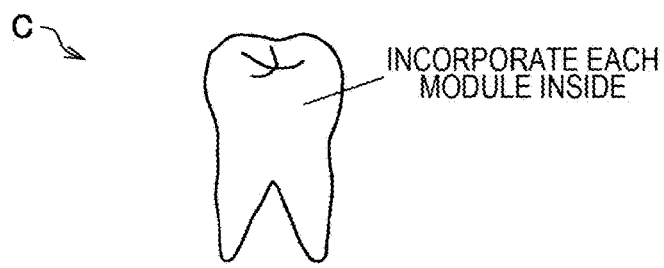

FIG. 13

CONDITIONS OF GUIDE STATE

☒ PLEASANT STRESS
　　☒ LEVEL 1　☐ LEVEL 2
☐ STRESS-FREE

---

CONDITIONS OF GENRE

☐ POPS　　☐ R&B
☐ JAZZ　　☐ ROCK
☐ CLASSIC　☐ POPULAR BALLAD
☒ ANY　　☐ CARTOON

---

CONDITIONS OF SEARCH RANGE

☐ WITHIN REGISTERED FRIENDS
☒ UNSPECIFIED
☐ RECOMMENDED
☐ ONLY MYSELF

FIG. 18

| CONTENT ID | SCENE | S' TIME-SERIES | VALUE OF S' UPON REPRODUCTION | CORRELATION COEFFICIENT UPON REPRODUCTION |
|---|---|---|---|---|
| 001 | SCENE A1 | | 35 | 0.77 |
| 002 | SCENE A2 | | 57 | 0.52 |
| 003 | SCENE B1 | | 139 | 0.97 |
| ⋮ | ⋮ | ⋮ | ⋮ | ⋮ |

.# STATE CONTROL APPARATUS, STATE CONTROL METHOD, AND STATE CONTROL SYSTEM

CROSS-REFERENCE TO RELATED APPLICATIONS

This application claims the benefit under 35 U.S.C. § 371 as a U.S. National Stage Entry of International Application No. PCT/JP2015/070424, filed in the Japanese Patent Office as a Receiving Office on Jul. 16, 2015, which claims priority to Japanese Patent Application Number JP 2014-190823, filed in the Japanese Patent Office on Sep. 19, 2014, each of which is hereby incorporated by reference in its entirety.

TECHNICAL FIELD

The present disclosure relates to a state control apparatus, a state control method, and a state control system.

BACKGROUND ART

A technology for reproducing content data based on biological information of a user has been developed. Examples of the technology for reproducing content data based on biological information of a user include, for example, a technology disclosed in the following Patent Literature 1.

CITATION LIST

Patent Literature

Patent Literature 1: JP 4396175B

DISCLOSURE OF INVENTION

Technical Problem

For example, in the case where the technology disclosed in Patent Literature 1 is used, a state of feeling of a user is analyzed based on biological information indicating a detection result of a heart rate, a pulse, a blood pressure, a body temperature, body motion, or the like, of the user, and content data corresponding to an analysis result is reproduced. Therefore, for example, in the case where the technology disclosed in Patent Literature 1 is used, it is possible to realize reproduction of content data suited for the biological information of the user.

However, for example, in the case where a state of feeling is analyzed by utilizing macro secondary change mainly involving a sympathetic nervous system such as a heart rate, a pulse, a blood pressure, a body temperature and body motion of a user as in the technology disclosed in Patent Literature 1, change of feeling of the user cannot be always predicted accurately.

The present disclosure proposes new and improved state control apparatus, state control method and state control system which can guide a state of feeling of a guide target to a predetermined set state.

Solution to Problem

According to the present disclosure, there is provided a state control apparatus including: an acquiring unit configured to acquire a state index indicating a state of target feeling based on biological information corresponding to the target feeling which is feeling of a target to be guided, the biological information being detected from a guide target whose state of feeling is to be guided; and a state control unit configured to determine a feeling guiding medium to be used for guiding the state of the target feeling based on the acquired state index and pattern information which is associated with the feeling guiding medium for guiding the state of the target feeling and which indicates a pattern of temporal change of the state index so that the state of the target feeling becomes a predetermined set state, and control the state of the target feeling of the guide target by performing processing relating to the determined feeling guiding medium. The biological information includes information indicating a detection result of an enzyme.

According to the present disclosure, there is provided a state control method executed by a state control apparatus, the state control method including: a step of acquiring a state index indicating a state of target feeling based on biological information corresponding to the target feeling which is feeling of a target to be guided, the biological information being detected from a guide target whose state of feeling is to be guided; and a step of determining a feeling guiding medium to be used for guiding the state of the target feeling based on the acquired state index and pattern information which is associated with the feeling guiding medium for guiding the state of the target feeling and which indicates a pattern of temporal change of the state index so that the state of the target feeling becomes a predetermined set state, and controlling the state of the target feeling of the guide target by performing processing relating to the determined feeling guiding medium. The biological information includes information indicating a detection result of an enzyme.

According to the present disclosure, there is provided a state control system including: a processing apparatus configured to perform processing using a feeling guiding medium for guiding a state of target feeling which is feeling of a target to be guided of a guide target whose state of feeling is to be guided; and a state control apparatus configured to guide the state of the target feeling of the guide target to a predetermined set state by causing the processing apparatus to perform the processing using the feeling guiding medium. The state control apparatus includes an acquiring unit configured to acquire a state index indicating the state of the target feeling based on biological information corresponding to the target feeling, the biological information being detected from the guide target, and a state control unit configured to determine the feeling guiding medium to be used for guiding the state of the target feeling based on the acquired state index and pattern information which is associated with the feeling guiding medium and which indicates a pattern of temporal change of the state index so that the state of the target feeling becomes a predetermined set state, and control the state of the target feeling of the guide target by performing processing relating to the determined feeling guiding medium, and the biological information includes information indicating a detection result of an enzyme.

Advantageous Effects of Invention

According to the present disclosure, it is possible to guide a state of feeling of a guide target to a predetermined set state.

Note that the effects described above are not necessarily limitative. With or in the place of the above effects, there

BRIEF DESCRIPTION OF DRAWINGS

FIG. 4 is an explanatory diagram for explaining an example of processing relating to the state control method according to the present embodiment.

FIG. 5 is an explanatory diagram for explaining an example of state control processing according to the present embodiment.

FIG. 11 is an explanatory diagram illustrating an example of an intraoral device according to the present embodiment.

FIG. 13 is an explanatory diagram illustrating an example of set conditions according to the present embodiment.

FIG. 18 is an explanatory diagram illustrating an example of a content list according to the present embodiment.

MODE FOR CARRYING OUT THE INVENTION

Figure 1:
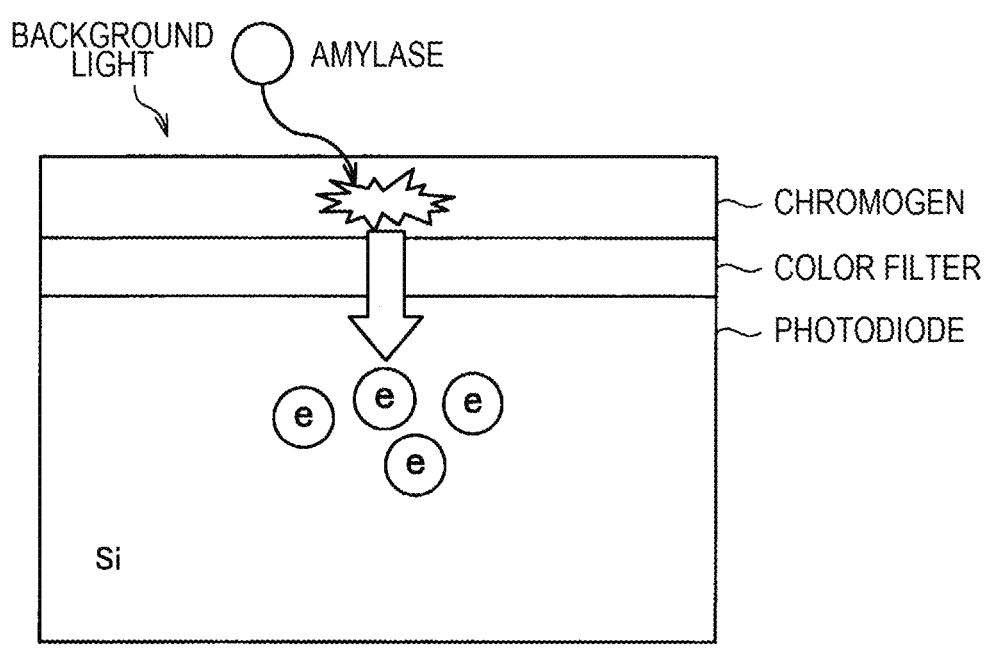
FIG. 1 is an explanatory diagram illustrating an example of an enzyme sensor (an example of a detecting device) according to the present embodiment.

Hereinafter, a preferred embodiment of the present disclosure will be described in detail with reference to the appended drawings. In this specification and the appended drawings, structural elements that have substantially the same function and structure are denoted with the same reference numerals, and repeated explanation of these structural elements is omitted.

Further, description will be provided below in the following order.
1. State control method according to present embodiment
2. State control apparatus according to present embodiment, state control system according to present embodiment
3. Program according to present embodiment

State Control Method According to Present Embodiment

First, a state control method according to the present embodiment will be described. The state control method according to the present embodiment will be described below using an example where a state control apparatus according to the present embodiment performs processing relating to the state control method according to the present embodiment.

[1] Outline of State Control Method According to Present Embodiment

The state control apparatus according to the present embodiment acquires a state index based on biological information corresponding to feeling of a target to be guided, which is detected from the target whose state of feeling is to be guided (acquisition processing). In the following description, the target whose state of feeling is to be guided will be referred to as a "guide target", and feeling of the target to be guided will be referred to as "target feeling".

Further, the state control apparatus according to the present embodiment determines a feeling guiding medium based on the acquired state index and pattern information associated with the feeling guiding medium so that the state of the target feeling becomes a predetermined set state and controls a state of the target feeling of the guide target by performing processing relating to the determined feeling guiding medium (state control processing). The state control apparatus according to the present embodiment performs processing relating to the feeling guiding medium corresponding to the state of the target feeling of the guide target, which is determined based on the state index corresponding to the guide target. The state control apparatus according to the present embodiment performs processing relating to the feeling guiding medium and controls the state of the target feeling of the guide target by guiding the state of the target feeling of the guide target to a predetermined state.

Here, examples of the guide target according to the present embodiment include, for example, a person. Further, the guide target according to the present embodiment may be animals other than a person.

Further, examples of the target feeling according to the present embodiment include, for example, one or more types of feeling out of "joy", "anger", "sorrow", "fun", "displeasure" and "pleasure". In the following description, a case will be described as an example where the target feeling according to the present embodiment is controlled to be put into a state of "pleasure" and "displeasure" of the guide target, that is, a state of stress is controlled using the state control method according to the present embodiment.

It is medically known that interaction of a sympathetic nervous system, an immune system and an endocrine system is caused inside the body, for example, by change of feeling of a person (for example, "joy", "anger", "sorrow", "fun", "displeasure" and "pleasure"). Further, as described above, in the case where the state of feeling is analyzed by utilizing macro secondary change mainly involving the sympathetic nervous system such as a heart rate, a pulse, a blood pressure, a body temperature and body motion, change of the feeling cannot be always predicted accurately.

Therefore, in the state control method according to the present embodiment, for example, information (data) indicating a detection result of an enzyme is used as the biological information according to the present embodiment corresponding to the target feeling. The information indicating the detection result of the enzyme can be obtained based on, for example, a detection result of an enzyme sensor (which will be described later).

Specifically, examples of the biological information according to the present embodiment include, for example, information indicating a detection result of salivary amylase (amylase included in saliva within the oral cavity. Hereinafter, simply referred to as "amylase") whose time constant of reaction to an external stimulus is within 1 (minute) (an example of a predetermined period). Further, in the case where the enzyme is salivary amylase, examples of the information indicating the detection result of the enzyme include, for example, data indicating an amount of amylase.

The salivary amylase is generated as a result of action of two systems of the sympathetic nervous system and the endocrine system, and is known as a stress biomarker whose time constant of reaction to an external stimulus (for example, stress) is within 1 (minute). Note that it is known that while the amount of amylase can fluctuate between day and night even in the case where the target is not put into a stress state, the amount of amylase rarely fluctuates with advancing aging. Therefore, the salivary amylase can be used as a stress marker which does not depend on an age group of the guide target by, for example, being subjected to calibration for fluctuation between day and night.

Note that the enzyme according to the present embodiment is not limited to amylase and may be an enzyme whose time constant of reaction to an external stimulus provided to the guide target is within a predetermined period (or an enzyme whose time constant is shorter than the predetermined period. The same will also apply hereinafter). That is, the state control apparatus according to the present embodiment can use information indicating a detection result of an enzyme whose time constant of reaction to an external stimulus provided to the guide target is within the predetermined period as the biological information according to the present embodiment corresponding to the target feeling. Further, the biological information according to the present embodiment corresponding to the target feeling is not limited to the enzyme as described above, and, for example, may be a substance in the body, such as hormone, whose time constant of reaction to an external stimulus provided to the guide target is within the predetermined period.

Here, the above-described predetermined period is, for example, 1 [minute]. Note that the above-described predetermined period is not limited to 1 [minute], and can be set at, for example, an arbitrary value corresponding to processing relating to the feeling guiding medium (an arbitrary value with which the target feeling can be guided using the feeling guiding medium).

An example in the case where the enzyme according to the present embodiment is salivary amylase and the biological information according to the present embodiment is information indicating a detection result of the salivary amylase will be described below.

Further, the biological information according to the present embodiment may include one or more pieces of other biological information based on a detection result of a heart rate, perspiration, or the like, of the guide target. That is, the biological information according to the present embodiment includes, for example, at least information indicating a detection result of an enzyme.

By using the information indicating the detection result of the enzyme as the biological information according to the present embodiment, it is possible to recognize change of a state of the target feeling more accurately than in the case where a state of feeling is analyzed by utilizing macro secondary change mainly involving the sympathetic nervous system such as a heart rate, a pulse, a blood pressure, a body temperature and body motion.

Further, in the case where the information indicating the detection result of the enzyme is used as the biological information according to the present embodiment, the biological information according to the present embodiment can be obtained from the guide target in a non-invasive manner. Therefore, in the case where the information indicating the detection result of the enzyme is used as the biological information according to the present embodiment, because the feeling of the guide target is made less likely to fluctuate by acquisition of the biological information according to the present embodiment, it is possible to recognize change of the state of target feeling more accurately.

Further, by using the information indicating the detection result of the enzyme whose time constant of reaction to an external stimulus is within the predetermined period as the biological information according to the present embodiment, it is possible to recognize the change of the state of the target feeling in a shorter period.

Examples of the state index according to the present embodiment include an activity level of the enzyme (hereinafter, referred to as an "enzyme activity level").

Note that the state index according to the present embodiment is not limited to the enzyme activity level. For example, the state index according to the present embodiment may be a result obtained by performing statistical processing such as multivariate analysis on the enzyme activity level also using one or more pieces of other biological information such as a heart rate and perspiration. A case will be described below using an example where the state index according to the present embodiment is the enzyme activity level.

The feeling guiding medium according to the present embodiment is a medium for guiding the state of the target feeling. Examples of the feeling guiding medium according to the present embodiment include, for example, content data indicating one or more pieces of content out of sound (including music), an image (a still image or a moving image) and text, and a program (computer program). Note that, in the following description, content data indicating the above-described various content and the program will be collectively referred to as "content data".

Further, examples of the processing relating to the feeling guiding medium according to the present embodiment include, for example, processing for reproducing content data, processing for causing an external apparatus to reproduce content data, processing for executing a program, processing for causing a program to be executed, or the like. A specific example of the processing relating to the feeling guiding medium according to the present embodiment will be described later.

The pattern information according to the present embodiment is data indicating a pattern of temporal change of the state index, and is associated with the feeling guiding medium according to the present embodiment. The pattern information according to the present embodiment is associated with the feeling guiding medium according to the present embodiment using, for example, a table (or a database). Note that the pattern information according to the present embodiment may be associated with the feeling guiding medium according to the present embodiment using data in an arbitrary form which can associate the pattern information with the feeling guiding medium.

In the following description, the pattern of temporal change of the state index indicated by the pattern information associated with the feeling guiding medium according to the present embodiment will be referred to as a "pattern of change of the feeling guiding medium" or a "feeing guiding medium having a pattern of change".

The pattern information according to the present embodiment corresponds to, for example, data obtained by expressing the state of the target feeling of the guide target in time series in the case where the processing relating to the associated feeling guiding medium is performed. That is, the pattern information according to the present embodiment indicates change of the state of the target feeling of the guide target, which is predicted in the case where the processing relating to the associated feeling guiding medium is performed.

The pattern information according to the present embodiment is, for example, set in advance. Further, the pattern information according to the present embodiment may be, for example, updated using the state index based on the biological information detected in the case where the processing relating to the associated feeling guiding medium is performed. In the case where the pattern information according to the present embodiment is updated using the state index based on the detected biological information, the pattern information according to the present embodiment becomes data indicating the past state indexes in time series.

As described above, the state control apparatus according to the present embodiment determines a feeling guiding medium so that, in the state control processing according to the present embodiment, the state of the target feeling becomes a predetermined set state. Here, examples of the predetermined state according to the present embodiment include, for example, a state corresponding to conditions of the guide state, set through operation by a user of the state control apparatus according to the present embodiment or the guide target. A setting example of the conditions of the guide state according to the present embodiment and an example of the predetermined state according to the present embodiment will be described later.

As an example of the processing relating to determination of the feeling guiding medium, the state control apparatus according to the present embodiment, for example, determines a feeling guiding medium to be used for guiding the state of the target feeling of the guide target among feeling guiding media having patterns of change opposite to the acquired pattern of the temporal change of the state index. The above-described example indicates that the state control apparatus according to the present embodiment guides the state of the target feeling of the guide target so that change inverse with change of the state of the target feeling of the guide target indicated by the acquired pattern of temporal change of the state index occurs in the guide target. Note that the example of the processing relating to determination of the feeling guiding medium in the state control processing according to the present embodiment will be described later.

The state control apparatus according to the present embodiment performs, for example, the above-described acquisition processing and the above-described state control processing as the processing relating to the state control method according to the present embodiment.

Here, in the above-described state control processing, the state control apparatus according to the present embodiment determines a feeling guiding medium based on the state index based on the biological information acquired through the above-described acquisition processing so that the state of the target feeling becomes a predetermined set state. Because the biological information according to the present embodiment includes information indicating the detection result of the enzyme such as salivary amylase, the state index acquired through the above-described acquisition processing indicates more accurate change of the state of the target feeling. Further, in the above-described state control processing, the state control apparatus according to the present embodiment controls the state of the target feeling of the guide target by performing processing relating to the determined feeling guiding medium.

Therefore, by the processing relating to the state control method according to the present embodiment being performed, it is possible to guide the state of the feeling of the guide target to the predetermined set state.

Note that the processing relating to the state control method according to the present embodiment is divided into the above-described acquisition processing and the above-described state control processing for convenience sake. Therefore, for example, the above-described acquisition processing and the above-described state control processing can be regarded as one processing in the processing relating to the state control method according to the present embodiment. Further, for example, the above-described acquisition processing and the above-described state control processing can be regarded as two or more processing (according to an arbitrary way of dividing the processing) in the processing relating to the state control method according to the present embodiment.

In the following description, a case will be mainly described using an example where the state control apparatus according to the present embodiment performs the above-described acquisition processing and the above-described state control processing as the processing relating to the state control method according to the present embodiment.

An example of the processing relating to the state control method according to the present embodiment will be more specifically described below. In the following description, a case will be described using an example where the target feeling according to the present embodiment is "pleasure" and "displeasure", the biological information according to the present embodiment is "information indicating a detection result of an enzyme", and the state index according to the present embodiment is an "enzyme activity level". Further, in the following description, a case will be mainly described using an example where the feeling guiding medium according to the present embodiment is "content data indicating music", and the processing relating to the feeling guiding medium according to the present embodiment is "reproduction processing of content data".

Note that, as described above, the feeling guiding medium according to the present embodiment may be data indicating an image, data indicating text or a program. Further, for example, in the processing relating to the state control method according to the present embodiment, by using a biomarker reflecting each feeling (for example, "joy", "anger", "sorrow" and "fun") other than feeling of "pleasure" and "displeasure" as the biological information according to the present embodiment, it is possible to guide each feeling in a similar manner.

[2] Example of Processing Relating to State Control Method According to Present Embodiment (1) Acquisition Processing The state control apparatus according to the present embodiment acquires a state index based on the biological information detected from the guide target.

(1-1) First Example of Acquisition Processing

The state control apparatus according to the present embodiment calculates a state index based on the biological information according to the detection result of the detecting device and acquires the state index.

Here, examples of the detecting device according to the present embodiment include, for example, a detecting device forming a detecting unit (which will be described later) of the state control apparatus according to the present embodiment, and an external detecting device connected to the state control apparatus according to the present embodiment in a wired or wireless manner.

Further, examples of the detecting device according to the present embodiment include, for example, an enzyme sensor. Further, the detecting device according to the present embodiment may further include one or more sensors for obtaining one or more pieces of other biological information such as a heart rate and perspiration of the guide target.

FIG. 1 is an explanatory diagram illustrating an example of the enzyme sensor (an example of the detecting device) according to the present embodiment. The enzyme sensor has, for example, a laminate structure of chromogen (Gal-G2–CNP), a color filter and an Si photodiode. Here, the color filter is a filter which transmits yellow light and does not transmit light of other color.

Further, the enzyme sensor according to the present embodiment may include, for example, an analog-to-digital (AD) converter, or the like, which converts an analog signal generated by the Si photodiode into a digital signal in a subsequent stage of the Si photodiode. Note that the above-described AD converter, or the like, may be an external device of the enzyme sensor according to the present embodiment.

In the case where amylase contacts chromogen of the enzyme sensor, hydrolysis reaction as indicated with the following chemical formula 1 proceeds.

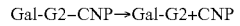  (Chemical formula 1)

During reaction indicated with the above-described chemical formula 1, amylase cuts a CNP side chain of the chromogen, and the chromogen which is originally white becomes yellow. The enzyme sensor performs photoelectric conversion on intensity of light generated through the reaction indicated with the above-described chemical formula 1 using the Si photodiode doped with impurities under background light. Data obtained by converting a signal by a photoelectron generated through photoelectric conversion by the AD converter, or the like, corresponds to the information indicating the detection result of the enzyme, that is, the biological information according to the detection result of the enzyme sensor.

Here, because light intensity changes according to the number of CNP side chains, it is possible to judge an amount of amylase from the signal by the photoelectron generated through photoelectric conversion.

Processing relating to calculation of the state index will be described using an example where the biological information is information indicating the amount of amylase (information indicating the detection result of the enzyme).

The state control apparatus according to the present embodiment calculates an enzyme activity level (an example of the state index. The same will also apply hereinafter) S with the following equation 1 using a value A indicated by the information indicating the amount of amylase. Here, "$A_{avg}$" indicated in the equation 1 is an average amount of amylase calculated while day and night are taken into account in a state where there is no external stimulus (stress) using the accumulated information indicating the amount of amylase.

$$S = (A - A_{avg})/A_{avg} \qquad \text{(equation 1)}$$

The state control apparatus according to the present embodiment calculates the state index by, for example, performing calculation indicated with the above-described equation 1 based on the biological information obtained from the detecting device. Note that the method for calculating the state index is not limited to the calculation indicated with the above-described equation 1, and the state index is calculated using a method corresponding to types of the biological information and the state index.

(1-2) Second Example of Acquisition Processing

The state control apparatus according to the present embodiment acquires the state index from an external apparatus through communication with the external apparatus.

The state control apparatus according to the present embodiment, for example, performs communication with the external apparatus through a communication unit (which will be described later) of the own apparatus (the state control apparatus according to the present embodiment. The same will also apply hereinafter) or an external communication device connected to the state control apparatus according to the present embodiment. The external apparatus calculates the state index by performing processing relating to calculation of the state index indicated in the above-described (1-1), and the state control apparatus according to the present embodiment acquires the state index calculated at the external apparatus through communication with the external apparatus. Note that the state control apparatus may perform communication with the external apparatus which calculates the state index via other apparatuses such as, for example, a relay apparatus.

The state control apparatus according to the present embodiment acquires the state index by performing, for example, the acquisition processing according to the first example indicated in the above-described (1-1) or the acquisition processing according to the second example indicated in the above-described (1-2).

(2) State Control Processing

The state control apparatus according to the present embodiment determines the feeling guiding medium based on the state index acquired in the processing of the above-described (1) (acquisition processing) and the pattern information. The state control apparatus according to the present embodiment controls the state of the target feeling of the guide target by performing processing relating to the determined feeling guiding medium.

Here, the state control apparatus according to the present embodiment, for example, performs state control processing based on various kinds of conditions set through operation by the user of the state control apparatus according to the present embodiment or the guide target.

Figure 2:
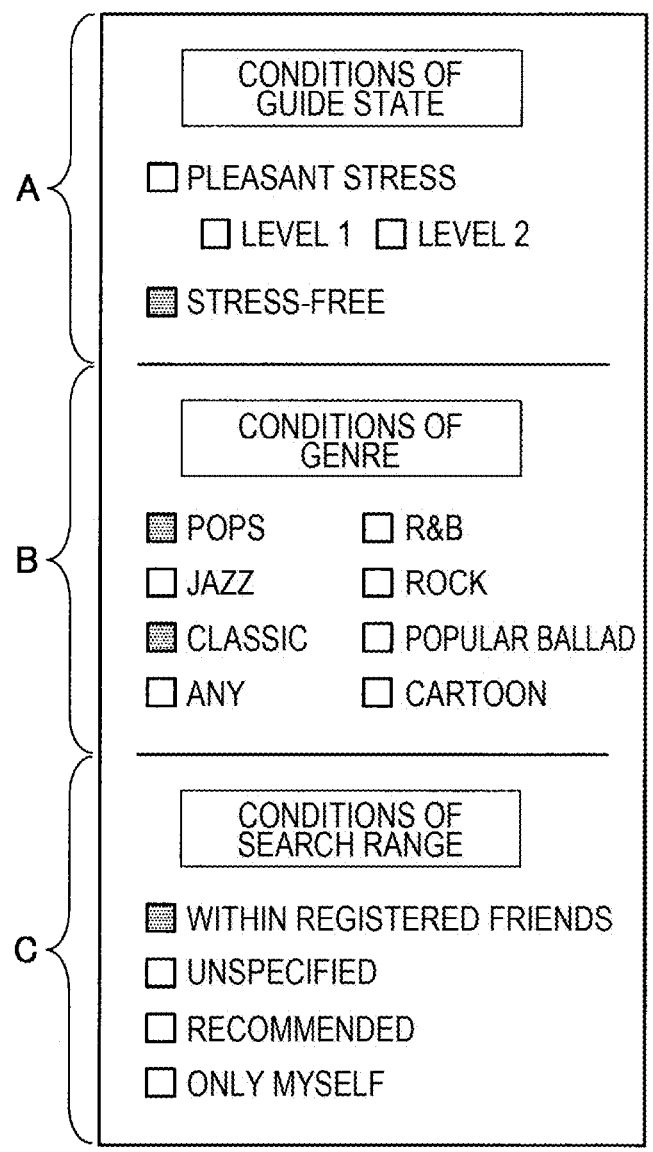
FIG. 2 is an explanatory diagram for explaining an example of processing relating to a state control method according to the present embodiment.

FIG. 2 is an explanatory diagram for explaining an example of the processing relating to the state control method according to the present embodiment and illustrates an example of a condition setting screen. FIG. 2 illustrates an example of a setting screen for setting conditions of the guide state (A illustrated in FIG. 2), conditions of a genre (B illustrated in FIG. 2) and conditions of a search range (C illustrated in FIG. 2).

Here, the conditions of the guide state (A illustrated in FIG. 2) are conditions as to which stress level the guide target is to be guided to. Examples of the conditions of the guide state include, for example, "pleasant stress" (there are a plurality of levels such as, for example, level 1 and level 2. For example, the greater level indicates greater stress) and "stress-free". Further, as the conditions of the guide state, a control value $S_a$ regarding to which level the enzyme activity level S is controlled to be and a threshold $S_L$ used for determining start of the state control processing are set. The values of the control value $S_a$ and the threshold $S_L$ may be fixed values set in advance or may be variable values which can be changed through operation by the user, or the like, of the state control apparatus according to the present embodiment.

Further, the conditions of a genre (B illustrated in FIG. 2) and the conditions of the search range (C illustrated in FIG. 2) are search conditions of the feeling guiding medium. Here, the search conditions of the feeling guiding medium according to the present embodiment may include conditions that do not limit a genre such as "any" illustrated in B in FIG. 2 and conditions that do not limit the search range such as "unspecified" illustrated in C in FIG. 2. That is, the search conditions of the feeling guiding medium according to the present embodiment can include conditions which do not limit the search range, or the like, of the feeling guiding medium.

Here, the operation with respect to the setting screen illustrated in FIG. 2 may be operation with respect to an operating unit (which will be described later) of the state control apparatus according to the present embodiment or may be operation with respect to arbitrary equipment of the guide target, such as a remote controller, a smartphone, a tablet type apparatus and a personal computer (PC).

Note that the condition setting screen according to the present embodiment is not limited to the example illustrated in FIG. 2. For example, one or both of a region for setting the conditions of a genre (B illustrated in FIG. 2) and a region for setting conditions of the search range (C illustrated in FIG. 2) may not be included in the condition setting screen according to the present embodiment.

(2-1) First Example of State Control Processing: Processing Relating to Start of Processing The state control apparatus according to the present embodiment starts control of the state of the target feeling of the guide target in the case where the state index acquired through the processing of the above-described (1) (acquisition processing) is greater than a predetermined set threshold (or in the case where the acquired state index becomes equal to or greater than the threshold. The same will also apply hereinafter).

Here, examples of the predetermined threshold according to the present embodiment include, for example, the threshold $S_L$ set for the set conditions of the guide state.

Figure 3:
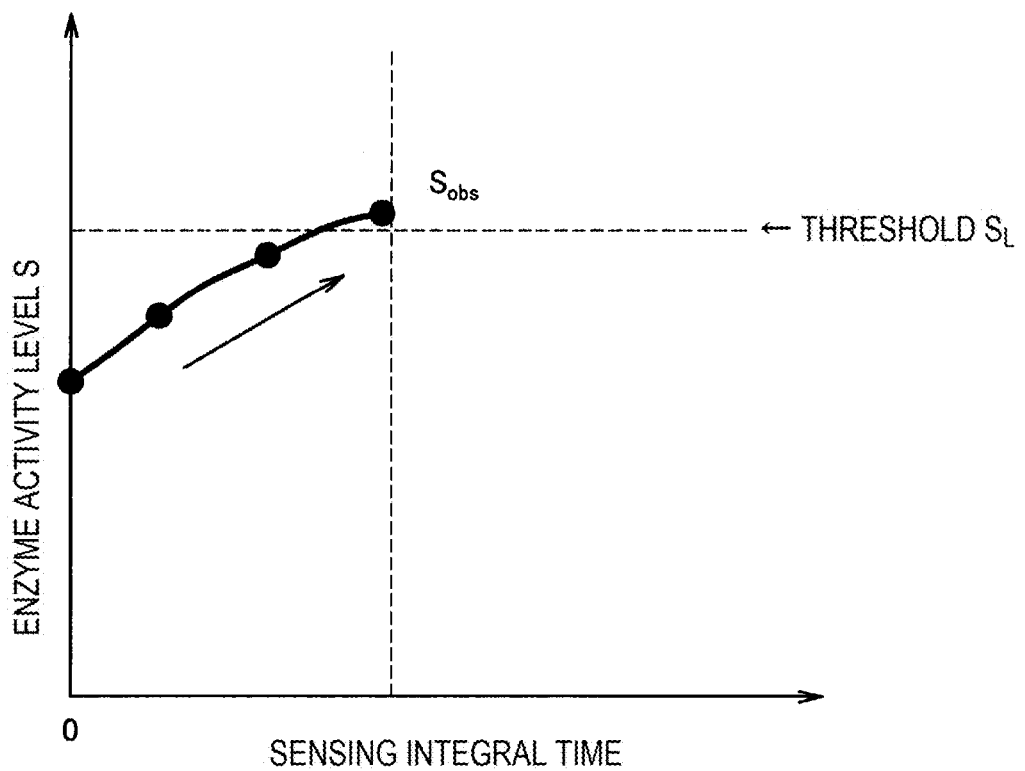
FIG. 3 is an explanatory diagram for explaining an example of state control processing according to the present embodiment.

FIG. 3 is an explanatory diagram for explaining an example of the state control processing according to the present embodiment. "$S_{obs}$" illustrated in FIG. 3 indicates the recently acquired enzyme activity level S (the same will also apply hereinafter).

For example, as illustrated in FIG. 3, the state control apparatus according to the present embodiment starts control of the state of the target feeling of the guide target in the case where the enzyme activity level S is greater than the threshold $S_L$.

(2-2) Second Example of State Control Processing: Processing 1 Relating to Determination of Feeling Guiding Medium The state control apparatus according to the present embodiment determines the feeling guiding medium to be used for guiding the state of the target feeling of the guide target among feeling guiding media which satisfy the set search conditions of the feeling guiding medium.

Here, for example, as illustrated in B in FIG. 2, the search conditions of the feeling guiding medium can include conditions indicating the search range of the feeling guiding medium. In the case where the search conditions include conditions indicating the search range of the feeling guiding medium, the state control apparatus according to the present embodiment determines the feeling guiding medium to be used for guiding the state of the target feeling of the guide target among the feeling guiding media included in the search range indicated by the set search conditions.

The state control apparatus according to the present embodiment specifies the feeling guiding media which satisfy the set search conditions of the feeling guiding medium by, for example, searching the whole search range indicated by the set search conditions. The state control apparatus according to the present embodiment determines the feeling guiding medium to be used for guiding the state of the target feeling of the guiding target among the specified feeling guiding media.

Note that the processing relating to determination of the feeling guiding medium which satisfies the set search conditions of the feeling guiding medium is not limited to the above-described processing.

For example, the state control apparatus according to the present embodiment may divide the search range indicated by the set search conditions into a plurality of ranges and perform processing for determining the feeling guiding medium which satisfies the set search conditions of the feeling guiding medium stepwise.

As a specific example, the state control apparatus according to the present embodiment first performs "first determination processing of determining the feeling guiding medium to be used for guiding the state of the target feeling of the guide target among feeling guiding media included in a first range out of the search range indicated by the set search conditions". In the case where the feeling guiding media which satisfy the set search conditions of the feeling guiding medium are specified in the first determination processing, the state control apparatus determines the feeling guiding medium to be used for guiding the state of the target feeling of the guide target among the specified feeling guiding media.

Here, in the case where the search range indicated by the set search conditions is "within registered friends", "unspecified" and "recommended" illustrated in FIG. 2, examples of the first range according to the present embodiment include, for example, the own apparatus (corresponding to "only myself" illustrated in FIG. 2). Note that the first range according to the present embodiment is not limited to the own apparatus. For example, in the case where the search range indicated by the set search conditions is "unspecified" illustrated in FIG. 2, the first range according to the present embodiment may be a smaller range such as "within registered friends" and "recommended" which allows a plurality of apparatuses to fall within the search range.

Further, in the case where the feeling guiding medium to be used for guiding the state of the target feeling is not determined through the first determination processing, the state control apparatus performs "second determination processing of determining the feeling guiding medium to be used for guiding the state of the target feeling of the guide target among feeling guiding media included in a second range other than the first range out of the search range indicated by the search conditions". In the case where the feeling guiding media which satisfy the set search conditions of the feeling guiding medium are specified through the second determination processing, the state control apparatus determines the feeling guiding medium to be used for guiding the state of the target feeling of the guide target among the specified feeling guiding media.

Here, in the case where the first range according to the present embodiment is the own apparatus, examples of the second range according to the present embodiment include a range other than the own apparatus out of the search range indicated by the set search conditions. Further, in the case where the first range according to the present embodiment is "within registered friends" and "recommended", examples of the second range according to the present embodiment include an arbitrary apparatus other than the apparatuses corresponding to "within registered friends" and "recommended".

Further, in the case where the feeling guiding medium to be used for guiding the state of the target feeling is not determined through the second determination processing, the state control apparatus according to the present embodiment, for example, changes the search range indicated by the search conditions. For example, in the case where the search range indicated by the set search conditions is "within registered friends" and "recommended" and the second range according to the present embodiment is a range other than the own apparatus out of the search range indicated by the set search conditions, the state control apparatus according to the present embodiment changes the search range by changing the search conditions to "unspecified".

The state control apparatus according to the present embodiment determines the feeling guiding medium to be used for guiding the state of the target feeling of the guide target among feeling guiding media included in the changed search range (third determination processing).

Note that the conditions included in the search conditions of the feeling guiding medium are not limited to the conditions indicating the search range of the feeling guiding medium. For example, the search conditions of the feeling guiding medium may include conditions of a genre as illustrated in C in FIG. 2.

In the case where the search conditions of the feeling guiding medium are conditions indicated in B in FIG. 2 and C in FIG. 2, the state control apparatus according to the present embodiment, for example, sets feeling guiding media which exist within the search range that matches the set conditions of the search range and which match the set conditions of a genre as feeling guiding media which satisfy the search conditions of the feeling guiding medium according to the conditions set in B in FIG. 2 and C in FIG. 2. The state control apparatus according to the present embodiment determines the feeling guiding medium to be used for guiding the state of the target feeling of the guide target among the feeling guiding media which satisfy the search conditions of the feeling guiding medium.

Note that, as described above, the search conditions of the feeling guiding medium according to the present embodiment can include conditions that do not limit the search range, or the like, of the feeling guiding medium. Therefore, there is also a case where the feeling guiding media which satisfy the set search conditions of the feeling guiding medium can be, for example, all feeling guiding media existing within the search range which can be searched by the state control apparatus according to the present embodiment.

FIG. 4 is an explanatory diagram for explaining an example of processing relating to the state control method according to the present embodiment and illustrates an example of a content list to be used for searching content data (an example of the feeling guiding medium. The same will also apply hereinafter). A in FIG. 4 illustrates an example of the content list, and B in FIG. 4 illustrates another example of the content list. FIG. 4 illustrates a case where content indicated by the content data is a "song".

As illustrated in A in FIG. 4, in the content list, a content ID is assigned to each content data. Further, in the content list, for example, a "genre", "name of song", a "songwriter", "time-series pattern data of enzyme activity level S", a "value of enzyme activity level S upon reproduction", a "correlation coefficient R upon reproduction" (a correlation coefficient between a pattern of the value of the enzyme activity level S of the content data and a value of the enzyme activity level S of the guide target which changes when a song is played. As the value is higher, it is expected that feeling of the guide target changes as indicated by the pattern of the song.), and the "cumulative number of times of reproduction" (an index of effect as with the correlation coefficient) are associated with each content ID. Here, the "time-series pattern data of enzyme activity level S" illustrated in FIG. 4 corresponds to an example of the pattern information according to the present embodiment.

The "time-series pattern data of enzyme activity level S", the "value of enzyme activity level S upon reproduction", the "correlation coefficient R upon reproduction" and the "cumulative number of times of reproduction" are updated, for example, every time the content data is reproduced.

Further, as illustrated in B in FIG. 4, the content list may further include additional items such as "tempo of song", "reproduction date and time" and "reproduction location".

The state control apparatus according to the present embodiment specifies content data which satisfies search conditions of the content data by referring to, for example, the content list as illustrated in FIG. 4.

Note that the example of the content list to be used for searching the content data is not limited to the examples illustrated in FIG. 4. For example, the content list according to the present embodiment may be a list in which the "content ID" is associated with the "time-series pattern data of enzyme activity level S", the "value of enzyme activity level S upon reproduction" and the "correlation coefficient R upon reproduction".

(2-3) Third Example of State Control Processing: Processing 2 Relating to Determination of Feeling Guiding Medium The state control apparatus according to the present embodiment determines the feeling guiding medium to be used for guiding the state of the target feeling of the guide target among feeling guiding media having patterns of change opposite to a pattern of temporal change of the state index acquired in the processing of the above-described (1) (acquisition processing).

Figure 6:
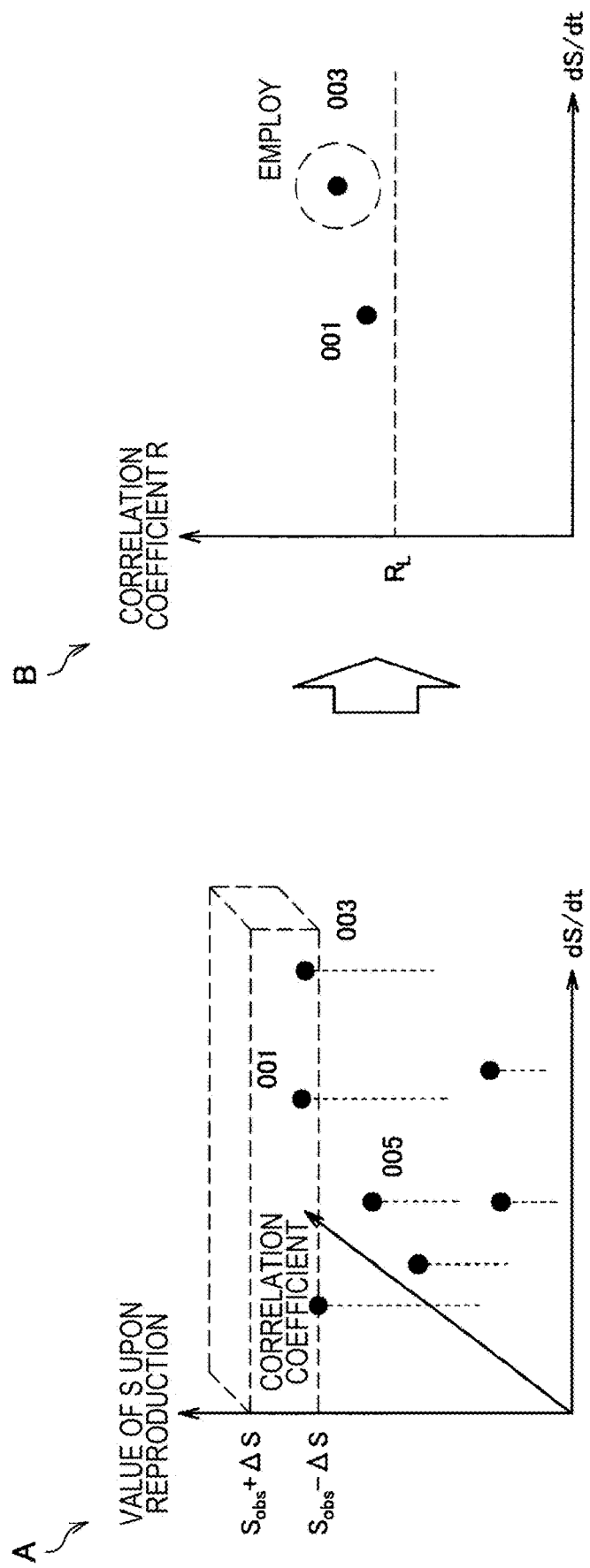
FIG. 6 is an explanatory diagram for explaining an example of state control processing according to the present embodiment.

FIG. 5 and FIG. 6 are explanatory diagrams for explaining an example of the state control processing according to the present embodiment.

As illustrated in A in FIG. 5, a case will be described using an example where the enzyme activity level S acquired in the processing of the above-described (1) (acquisition processing) has a pattern of soaring temporal change as illustrated in FIG. 3 in the case where there is content data whose content ID is "001", "002", . . . . Here, for example, in the case where the state control processing according to the second example indicated in the above-described (2-2) is performed, the content data illustrated in A in FIG. 5 corresponds to a feeling guiding medium which satisfies the set search conditions of the feeling guiding medium.

In the above-described case, the state control apparatus according to the present embodiment sets content data having a pattern of change opposite to the acquired pattern of temporal change of the enzyme activity level S as a candidate for content data to be used for guiding the state of the target feeling of the guide target among the content data illustrated in A in FIG. 5. In the following description, the candidate for the content data to be used for guiding the state of the target feeling of the guide target may be referred to as "candidate content data".

In the example illustrated in FIG. 5, as illustrated in B in FIG. 5, the content data whose content ID is "001", "003", "005", . . . is made the candidate content data.

In the case where the candidate content data is specified, for example, as illustrated in A in FIG. 6, the state control apparatus according to the present embodiment extracts content data whose value of the enzyme activity level S upon reproduction falls within a predetermined range ($S_{obs} \pm \Delta S$) in triaxial space of time variation dS/dt of the enzyme activity level S within a reproduction period t1 (for example, 30 [seconds]), the value of the enzyme activity level S upon reproduction and the correlation coefficient R. A in FIG. 6 illustrates an example where the content data whose content ID is "001" and "003" is extracted.

The state control apparatus according to the present embodiment then, for example, as illustrated in B in FIG. 6, determines content data whose correlation coefficient R is equal to or greater than a threshold $R_L$ (or the correlation coefficient R is greater than the threshold $R_L$) and whose value of the time variation dS/dt is greater as content data to be used for guiding the state of the target feeling of the guide target. B in FIG. 6 illustrates an example where the content data whose content ID is "003" is determined as the content data to be used for guiding the state of the target feeling of the guide target.

Here, the value of the enzyme activity level S upon reproduction is used as an index, for example, in order to determine content data appropriate for a stress state upon determination of the content data. Further, the correlation coefficient R is used as an index, for example, because it can be predicted that stable state change is expected.

Further, the "$\Delta S$", the "threshold $R_L$" and the "time variation dS/dt" are, for example, determined while depending on guide conditions set in A in FIG. 2. For example, in the case where the conditions of "stress-free" are set as the guide conditions, in order to realize feeling guidance instantaneously, it is set such that $\Delta S=0.1 \cdot S$, $R_L=0.8$, and dS/dt=max value. Further, for example, in the case where the conditions of "pleasant stress" are set as the guide conditions, it may be set such that $\Delta S=0.5 \cdot S$, $R_L=0.5$, and dS/dt may be set at an arbitrary value.

For example, through the processing described with reference to FIG. 5 and FIG. 6, as illustrated in C in FIG. 5, the content data whose content ID is "003" is determined as the content data to be used for guiding the state of the target feeling of the guide target.

Note that the processing relating to determination of the content data to be used for guiding the state of the target feeling of the guide target is not limited to the processing described with reference to FIG. 5 and FIG. 6. For example, the state control apparatus according to the present embodiment can perform processing as described below.

First, content data whose correlation coefficient R is equal to or greater than the threshold $R_L$ (or content data whose correlation coefficient R is greater than the threshold $R_L$) is extracted among the candidate content data.

Then, content data whose enzyme activity level S upon reproduction falls within a predetermined range ($S_{obs} \pm \Delta S$) and whose value of the time variation dS/dt is greater is determined as the content data to be used for guiding the state of the target feeling of the guide target.

(2-4) Fourth Example of State Control Processing: Processing Relating to Switching of Feeling Guiding Medium In the case where control by the processing relating to the determined feeling guiding medium is started, the state control apparatus according to the present embodiment can switch the feeling guiding medium to be used for controlling the state of the target feeling of the guide target to control the state of the target feeling of the guide target.

More specifically, the state control apparatus according to the present embodiment redetermines the feeling guiding medium based on time elapsed since control by the processing relating to the determined feeling guiding medium is started and pattern information associated with the determined feeling guiding medium so that the state of the target feeling becomes a predetermined state.

Here, the redetermined feeling guiding medium is, for example, a feeling guiding medium having a pattern of change opposite to a pattern of temporal change of a state index in the pattern information associated with the determined feeling guiding medium.

As an example, the state control apparatus according to the present embodiment, for example, sets content data having a pattern of change opposite to the pattern of temporal change of the acquired enzyme activity level S as candidate content data in a similar manner to the state control processing according to the third example indicated in the above-described (2-3). The state control apparatus according to the present embodiment, for example, redetermines the content data to be used for guiding the state of the target feeling of the guide target among the candidate content data in a similar manner to the state control processing according to the third example indicated in the above-described (2-3).

Further, the state control apparatus according to the present embodiment switches the feeling guiding medium to be used for controlling the state of the target feeling of the guide target from the feeling guiding media being used (that is, feeling guiding media determined previously) to the redetermined feeling guiding medium to control the state of the target feeling of the guide target. The state control apparatus according to the present embodiment, for example, controls the state of the target feeling of the guide target by switching the processing relating to the feeling guiding medium to be executed from processing relating to the feeling guiding media being used to processing relating to the redetermined feeling guiding medium.

Figure 7:
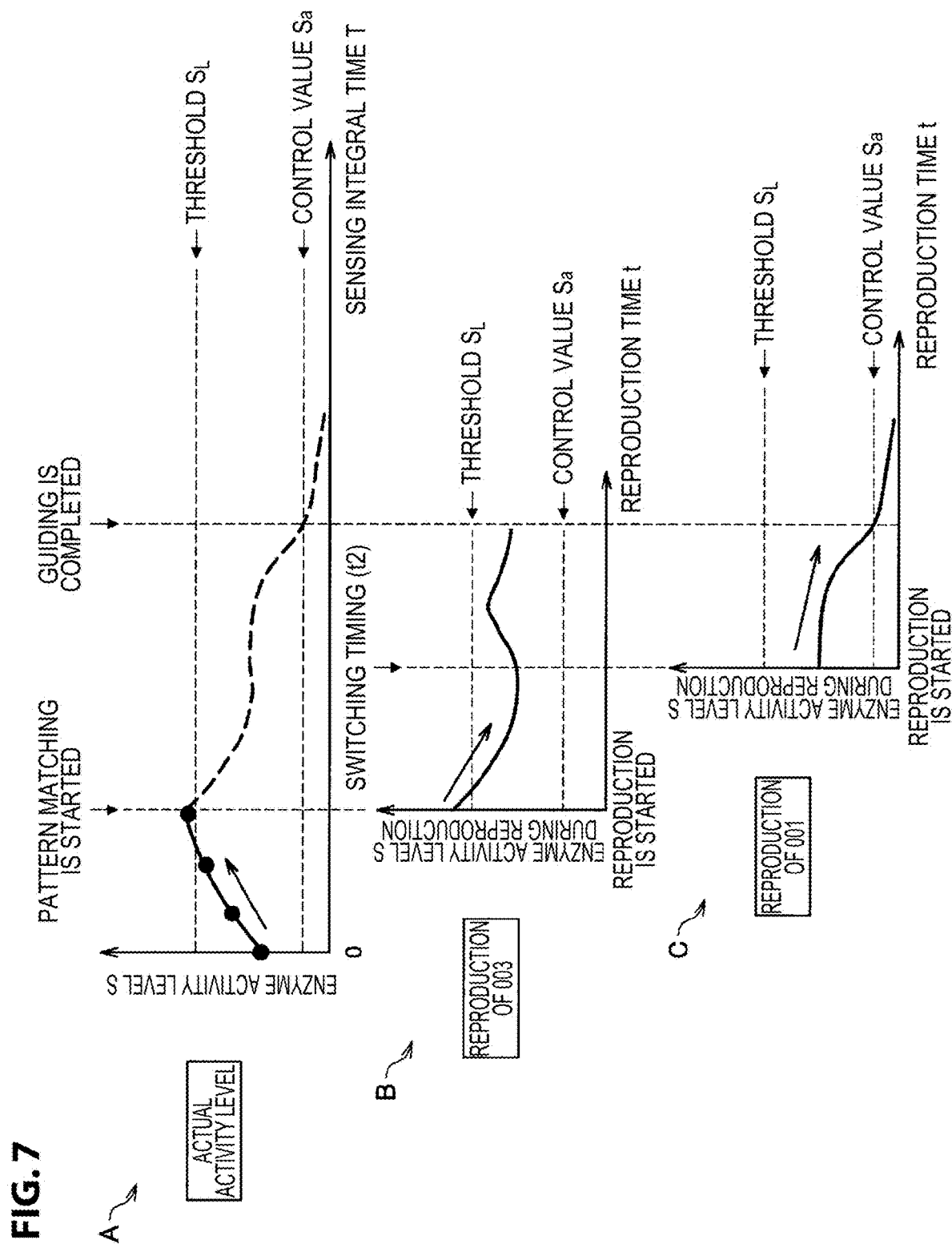
FIG. 7 is an explanatory diagram for explaining an example of state control processing according to the present embodiment.
Figure 8:
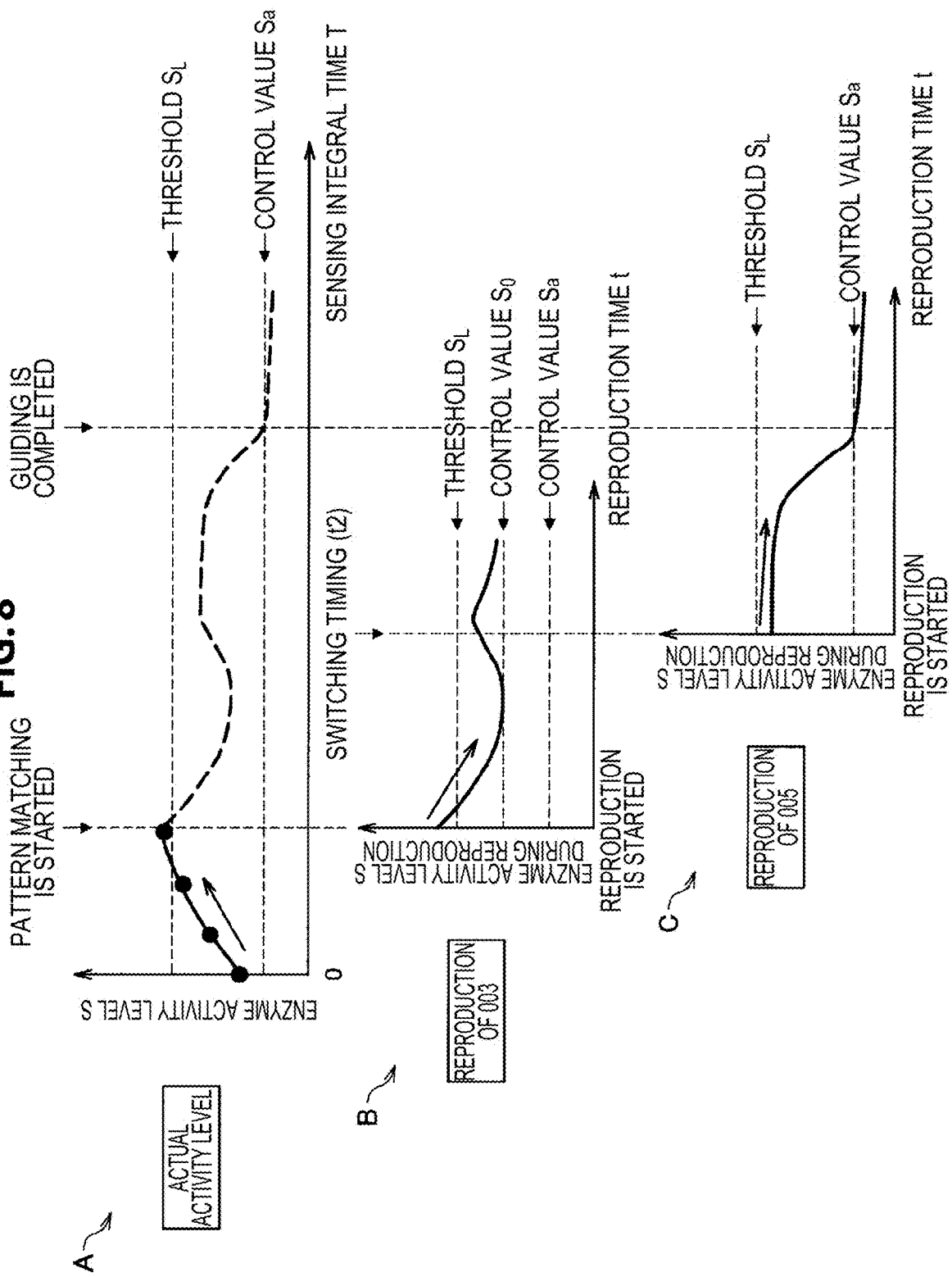
FIG. 8 is an explanatory diagram for explaining an example of state control processing according to the present embodiment.

FIG. 7 and FIG. 8 are explanatory diagrams for explaining an example of the state control processing according to the present embodiment. FIG. 7 illustrates an example of control of the state of the target feeling of the guide target through the state control processing in the case where the conditions of "stress-free" are set as the guide conditions. Further, FIG. 8 illustrates an example of control of the state of the target feeling of the guide target through the state control processing in the case where the conditions of "pleasant stress" are set as the guide conditions.

A in FIG. 7 and A in FIG. 8 illustrate temporal change of the enzyme activity level S of the guide target. Further, B and C in FIG. 7, and B and C in FIG. 8 illustrate examples of a pattern of temporal change of the enzyme activity level S indicated by the pattern information associated with the content data.

In the case where control by the processing relating to the determined feeling guiding medium is started (corresponding to "pattern matching is started" illustrated in FIG. 7 and FIG. 8), the determined content data is reproduced (B in FIG. 7, B in FIG. 8). In the case where the acquired enzyme activity level S does not reach the control value $S_a$ through reproduction of the determined content data, the state control apparatus according to the present embodiment, for example, performs processing indicated in the following (a) and (b).

(a)

In the case where the conditions of "stress-free" are set as the guide conditions, as illustrated in B in FIG. 7, the state control apparatus according to the present embodiment determines the content data again at time t2 at which the enzyme activity level S indicated by the pattern information associated with the content data being reproduced starts increasing. The state control apparatus according to the present embodiment then positively reduces the enzyme activity level S of the guide target by switching the content data to the content data determined again and reproducing the content data. FIG. 7 illustrates an example where content data whose content ID is "001" is reproduced as illustrated in C in FIG. 7.

In the example illustrated in FIG. 7, as illustrated in C in FIG. 7, by the redetermined content data being reproduced, the acquired enzyme activity level S reaches the control value $S_a$. Therefore, in the example illustrated in FIG. 7, content data is not further switched.

Note that, in the case where the acquired enzyme activity level S does not reach the control value $S_a$ even if the redetermined content data is reproduced, the state control apparatus according to the present embodiment redetermines the content data again and further switches the content data to the redetermined content data and reproduces the content data.

(b)

In the case where the conditions of "pleasant stress" are set as the guide conditions, as illustrated in B in FIG. 8, the state control apparatus according to the present embodiment, for example, determines the content data again at a time point at which a times of a pattern extreme value $S_0$ is reached since the song is reproduced. The state control apparatus according to the present embodiment then switches the content data to the content data determined again and reproduces the content data. Here, the value of "α" is, for example, a value according to a level of the conditions of "pleasant stress" (such as, for example, 0.3 in the case of level 1 and 0.5 in the case of level 2). FIG. 8 illustrates an example where content data whose content ID is "005" is reproduced as illustrated in C in FIG. 8.

In the example illustrated in FIG. 8, as illustrated in C in FIG. 8, by the redetermined content data being reproduced, the acquired enzyme activity level S reaches the control value $S_a$. Therefore, in the example illustrated in FIG. 8, the content data is not further switched.

Note that, in the case where the acquired enzyme activity level S does not reach the control value $S_a$ even if the redetermined content data is reproduced, the state control apparatus according to the present embodiment redetermines the content data again and switches the content data to the redetermined content data and reproduces the content data.

For example, the state control apparatus according to the present embodiment can, for example, guide the state of the target feeling of the guide target to a set desired state without making the guide target aware of being guided by performing processing indicated in the above-described (a) and (b) and selectively switching the content data to be reproduced. Note that it goes without saying that the example of the processing relating to switching of the feeling guide medium is not limited to the processing indicated in the above-described (a) and (b).

(2-5) Fifth Example of State Control Processing: Processing Relating to Updating of Pattern Information The state control apparatus according to the present embodiment updates the pattern information associated with the determined feeling guiding medium based on the acquired state index.

The state control apparatus according to the present embodiment, for example, updates the pattern information associated with the content data using a pattern of temporal change of the enzyme activity level S of the guide target caused by reproduction of the content data after reproduction of the content data is finished.

By the pattern information being updated as described above, the pattern information associated with the feeling guiding medium is updated to the latest state.

(2-6) Sixth Example of State Control Processing: Processing Relating to Notification of State The state control apparatus according to the present embodiment may, for example, give notification of the state of the target feeling of the guide target. The state control apparatus according to the present embodiment gives notification of the state of the target feeling of the guide target through, for example, "auditory notification by causing a sound output device such as a speaker to output sound corresponding to the state of the target feeling", "visual notification by causing a display device to display an image corresponding to the state of the target feeling or causing a light emitting device such as a light-emitting diode (LED) to emit light of color corresponding to the state of the target feeling", "olfactory notification by causing a device to output odor corresponding to the state of the target feeling" or "notification using combination of these".

By the state control apparatus according to the present embodiment giving notification of the state of the target feeling of the guide target, for example, it becomes possible to convey the state of feeling of a disabled person, a patient, a pet, or the like, who have difficulty in conveying feeling of "pleasure", "displeasure", or the like, by words to people around them.

(2-7) Seventh Example of State Control Processing

The state control apparatus according to the present embodiment can also perform processing which is combination of two or more processing out of the state control processing according to the first example indicated in the above-described (2-1) to the sixth example indicated in the above-described (2-6).

The state control apparatus according to the present embodiment, for example, performs the processing of the above-described (1) (acquisition processing) and the processing of the above-described (2) (state control processing) as the processing relating to the state control method according to the present embodiment.

Note that, as described above, while the processing relating to the state control method according to the present embodiment is divided into the processing of the above-described (1) (acquisition processing) and the processing of the above-described (2) (state control processing) for convenience sake, the processing relating to the state control method according to the present embodiment is not limited to the processing of the above-described (1) (acquisition processing) and the processing of the above-described (2) (state control processing).

Figure 9:
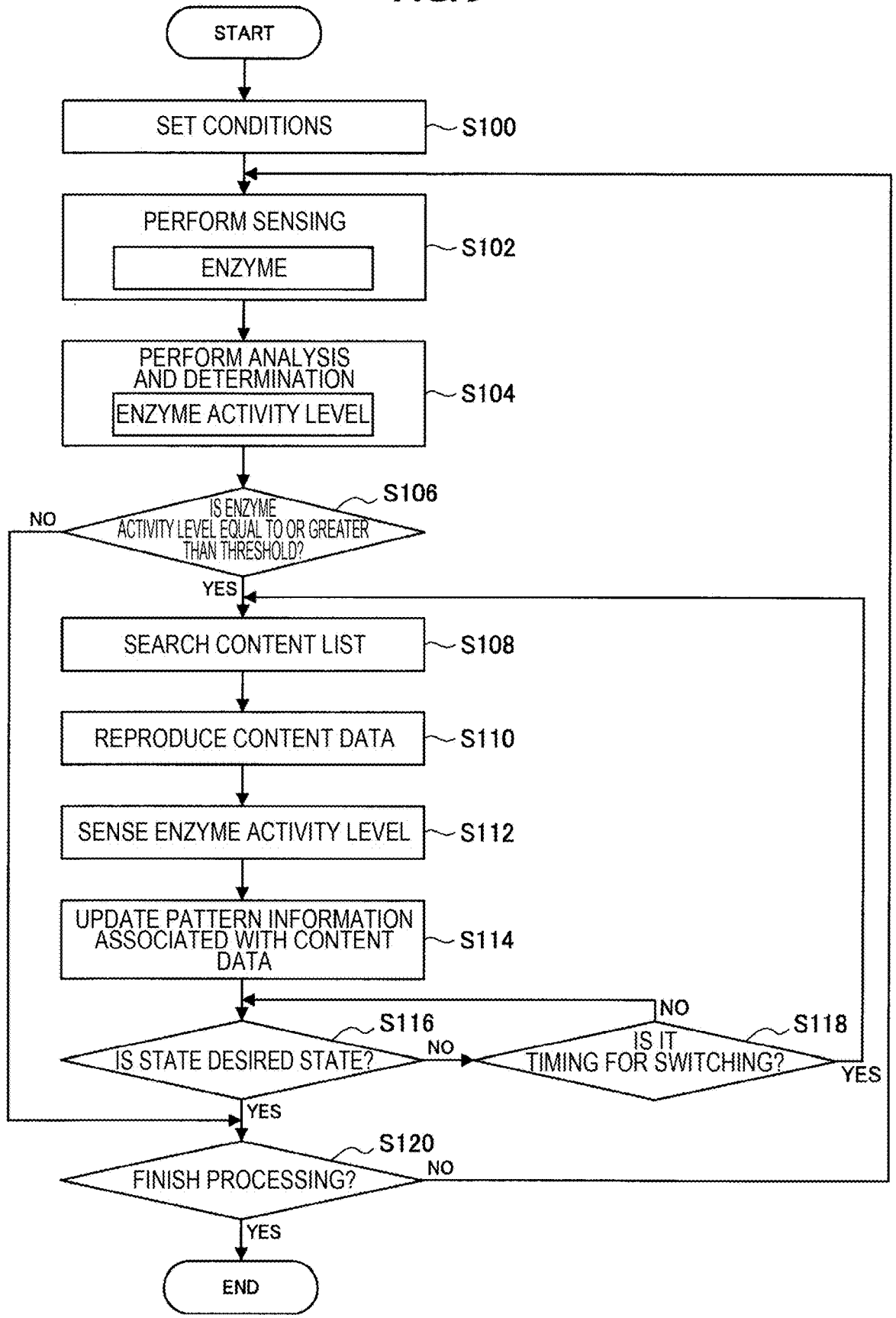
FIG. 9 is a flowchart illustrating an example of processing relating to the state control method according to the present embodiment.

[3] Specific Example of Processing Relating to State Control Method According to Present Embodiment FIG. 9 is a flowchart illustrating an example of the processing relating to the state control method according to the present embodiment. Here, in FIG. 9, the processing in step S104 corresponds to an example of the processing of the above-described (1) (acquisition processing), and step S106 to S120 corresponds to an example of the processing of the above-described (2) (state control processing).

The state control apparatus according to the present embodiment sets conditions (S100). The state control apparatus according to the present embodiment, for example, sets conditions of the guide state (for example, the "conditions of a guide state" illustrated in A in FIG. 2) and search conditions of the feeling guiding medium (for example, the "conditions of a genre" illustrated in B in FIG. 2 and the "conditions of a search range" illustrated in C in FIG. 2) based on the operation with respect to the setting screen as illustrated in FIG. 2.

The state control apparatus according to the present embodiment sequentially detects an enzyme using the enzyme sensor (S102).

The state control apparatus according to the present embodiment acquires the enzyme activity level S based on information indicating the detection result of the enzyme obtained through detection in step S102 (S104). The state control apparatus according to the present embodiment acquires the enzyme activity level S by, for example, performing the acquisition processing according to the first example indicated in the above-described (1-1) and calculating the enzyme activity level S. Here, while not illustrated in FIG. 9, the processing in step S104 is performed, for example, every time detection is performed in step S102.

The state control apparatus according to the present embodiment determines whether or not the enzyme activity level S is equal to or greater than the threshold $S_L$ (S106).

In the case where it is not determined in step S106 that the enzyme activity level S is equal to or greater than the threshold $S_L$, the state control apparatus according to the present embodiment performs processing in step S120 which will be described later.

Further, in the case where it is determined in step S106 that the enzyme activity level S is equal to or greater than the threshold $S_L$, the state control apparatus according to the present embodiment searches the content list and determines the content data to be used for guiding the state of the target feeling of the guide target (S108).

Figure 10:
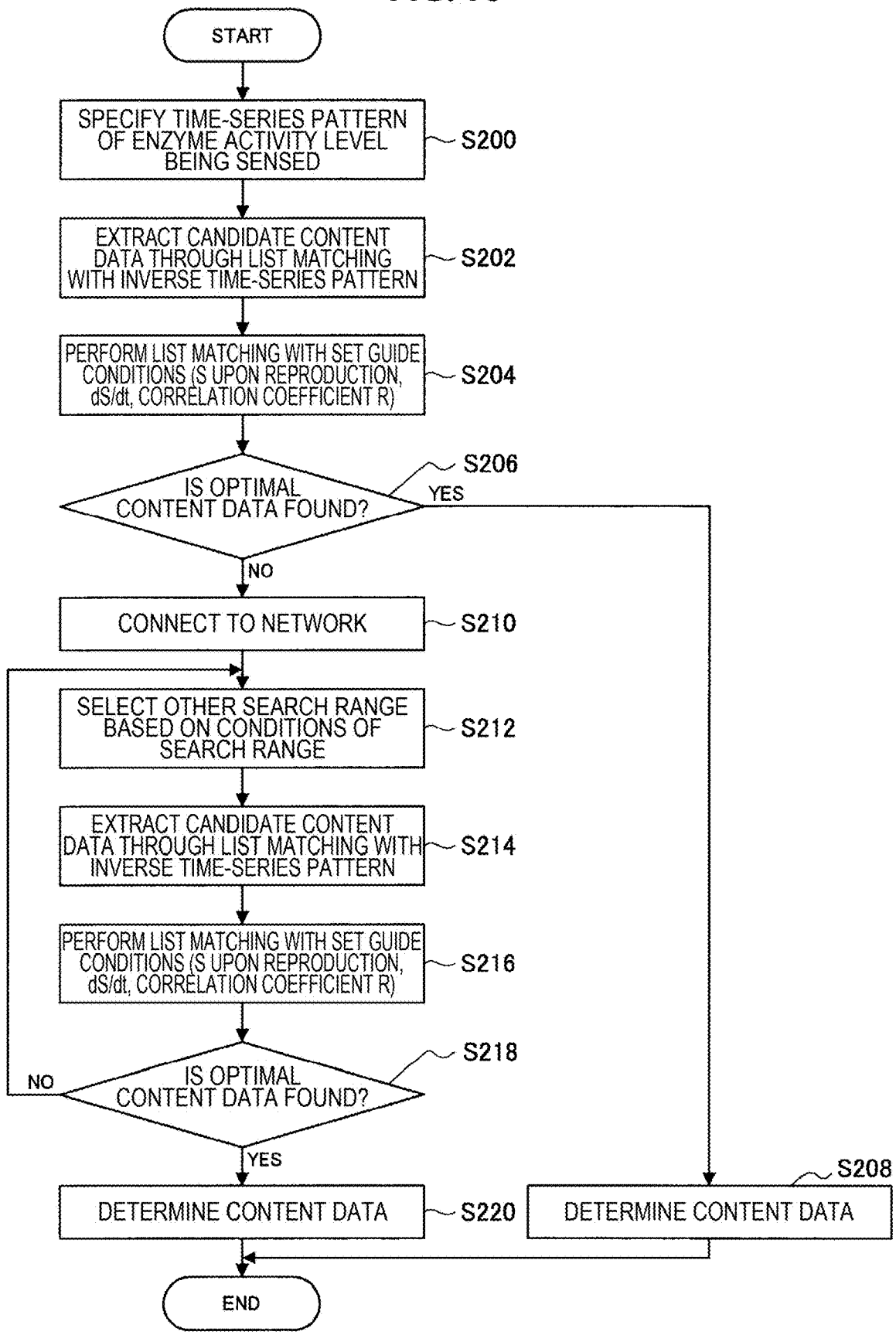
FIG. 10 is a flowchart illustrating an example of processing relating to the state control method according to the present embodiment.

FIG. 10 is a flowchart illustrating an example of the processing relating to the state control method according to the present embodiment and illustrates an example of the processing relating to determination of the content data to be used for guiding the state of the target feeling of the guide target.

The state control apparatus according to the present embodiment specifies a time-series pattern of the enzyme activity level S, for example, as illustrated in FIG. 3 using the enzyme activity level S acquired in step S104 from the enzyme sequentially detected in S102 in FIG. 9 (S200).

The state control apparatus according to the present embodiment extracts content data having a pattern inverse with the time-series pattern of the enzyme activity level S as the candidate content data from the content list as illustrated in FIG. 4 (S202).

The state control apparatus according to the present embodiment matches the set guide conditions to the list of the candidate content data (S204). The state control apparatus according to the present embodiment performs the state control processing according to the third example indicated in the above-described (2-3) in step S204 and finds the content data to be used for guiding the state of the target feeling of the guide target among the candidate content data. Here, for example, the state control apparatus according to the present embodiment finds the content data to be used for guiding the state of the target feeling of the guide target while setting the own apparatus as a search range.

The state control apparatus according to the present embodiment determines whether or not optimal content data to be used for guiding the state of the target feeling of the guide target is found (S206).

In the case where optimal content data is found in step S206, the state control apparatus according to the present embodiment determines the found content data as the content data to be used for guiding the state of the target feeling of the guide target (S208). The state control apparatus according to the present embodiment then finishes the processing illustrated in FIG. 10.

Further, in the case where optimal content data is not found in step S206, the state control apparatus according to the present embodiment connects to a network (S210) and selects another search range based on the set conditions of the search range (such as, for example, "within registered friends" illustrated in C in FIG. 2) (S212). Note that the state control apparatus according to the present embodiment can change the set conditions of the search range as with the state control processing according to the second example indicated in the above-described (2-2).

By another search range being selected as in step S212, for example, it is possible to utilize content data which satisfies the set conditions of a genre, and for which effect on other users has been verified, as the content data to be used for guiding the state of the target feeling of the guide target. Therefore, by another search range being selected as in step S212, more effective guidance of the state of the target feeling is expected to be realized, and it is possible to allow a person, or the like, who is a guide target to experience unexpected discovery or have fun which cannot be experienced through simple mechanical control.

As in step S202, the state control apparatus according to the present embodiment extracts content data having a pattern inverse with the time-series pattern of the enzyme activity level S as the candidate content data from the content list within the search range selected in step S212 (S214).

As in step S204, the state control apparatus according to the present embodiment matches the set guide conditions to the list of the candidate content data and finds the content data to be used for guiding the state of the target feeling of the guide target (S216).

The state control apparatus according to the present embodiment determines whether or not optimal content data to be used for guiding the state of the target feeling of the guide target is found (S218).

In the case where optimal content data is not found in step S218, the state control apparatus according to the present embodiment repeats the processing from step S212.

Further, in the case where optimal content data is found in step S218, the state control apparatus according to the present embodiment determines the found content data as the content data to be used for guiding the state of the target feeling of the guide target (S220). The state control apparatus according to the present embodiment then finishes the processing illustrated in FIG. 10.

The state control apparatus according to the present embodiment determines the content data to be used for guiding the state of the target feeling of the guide target by, for example, performing the processing illustrated in FIG. 10 in step S108 in FIG. 9. Note that it goes without saying that the processing in step S108 in FIG. 9 is not limited to the example illustrated in FIG. 10.

Referring to FIG. 9 again, an example of the processing relating to the state control method according to the present embodiment will be described. The state control apparatus according to the present embodiment reproduces the content data determined in step S108 (S110). Further, the state control apparatus according to the present embodiment senses the enzyme activity level S (S112). The state control apparatus according to the present embodiment then updates the pattern information associated with the content data being reproduced based on the enzyme activity level S being sensed (S114).

The state control apparatus according to the present embodiment determines whether or not the enzyme activity level S is in a desired state (S116). In the case where, for example, the enzyme activity level S is equal to or less than the control value $S_a$ (or the enzyme activity level S is less than the control value $S_a$), the state control apparatus according to the present embodiment determines that the enzyme activity level S is in the desired state.

In the case where it is not determined in step S116 that the enzyme activity level S is in the desired state, the state control apparatus according to the present embodiment determines whether or not it is a timing for switching (S118). The state control apparatus according to the present embodiment determines whether or not it is a timing for switching by, for example, performing the state control processing according to the fourth example indicated in the above-described (2-4).

In the case where it is not determined in step S118 that it is a timing for switching, the state control apparatus according to the present embodiment, for example, repeats the processing from step S116.

In the case where it is determined in step S118 that it is a timing for switching, the state control apparatus according to the present embodiment, for example, repeats the processing from step S108.

In the case where it is determined in step S116 that the enzyme activity level S is in a desired state, or in the case where it is not determined in step S106 that the enzyme activity level S is equal to or greater than the threshold $S_L$, the state control apparatus according to the present embodiment determines whether or not to finish the processing (S120). For example, in the case where a signal corresponding to the operation of finishing the processing, such as depression of a button for finishing the processing, is detected, the state control apparatus according to the present embodiment determines to finish the processing.

In the case where it is not determined in step S120 to finish the processing, the state control apparatus according to the present embodiment, for example, repeats the processing from step S102. Further, in the case where it is not determined in step S120 to finish the processing, the state control apparatus according to the present embodiment finishes the processing illustrated in FIG. 9.

The state control apparatus according to the present embodiment, for example, performs the processing illustrated in FIG. 9 as the processing relating to the state control method according to the present embodiment.

Note that the example of the processing relating to the state control method according to the present embodiment is not limited to the example illustrated in FIG. 9.

For example, the state control apparatus according to the present embodiment can allow the third party to recognize change of the state of "pleasure" and "displeasure" of the guide target in real time by outputting the enzyme activity level S sensed in step S112 to a light emitting device such as an LED and external equipment such as a smartphone.

Further, the state control apparatus according to the present embodiment does not have to perform, for example, the processing in step S114 illustrated in FIG. 9.

[4] Application Example of State Control Method According to Present Embodiment An application example of the state control method according to the present embodiment will be described next.

[4-1] First Application Example: Stress Reduction Through Music Using Intraoral Device As a first application example, an application example relating to stress reduction through music using an intraoral device will be described. The first application example can be implemented with, for example, an apparatus such as an intraoral device which can be used by being worn on the guide target (hereinafter, referred to as an "apparatus at the guide target side") and a state control system having the state control apparatus according to the present embodiment. Note that the first application example can be also implemented in the case where the intraoral device plays a role of the state control apparatus according to the present embodiment. In the following description, a case will be described as an example where the first application example is implemented with the state control system.

FIG. 11 is an explanatory diagram illustrating an example of the intraoral device according to the present embodiment. A in FIG. 11 illustrates an example of a mouthpiece type intraoral device. Further, B in FIG. 11 illustrates an example of a false tooth type (for example, there can be a full-coverage type and a partial-coverage type) intraoral device, and C in FIG. 11 illustrates an example of an implant type intraoral device.

For example, as illustrated in FIG. 11, at the intraoral device according to the present embodiment, various kinds of modules such as an enzyme sensor, a pressure sensor, a motion sensor (for example, an acceleration sensor), a position sensor (such as, for example, a global positioning system (GPS) module and a recording medium which stores map data), a power storage module, a communication device (for example, a radio frequency (RF) module), a bone-conduction module and a power generation module are provided on a substrate. Each module of the intraoral device according to the present embodiment may be, for example, detachable from the substrate. In the case where each module is detachable from the substrate, it is possible to realize the intraoral device having a function according to the state of the guide target or meeting the request of the guide target.

Further, the intraoral device according to the present embodiment includes one or more processors configured with an arithmetic circuit such as, for example, a micro processing unit (MPU). At the intraoral device according to the present embodiment, various kinds of processing relating to the state control method according to the present embodiment are initiatively performed by, for example, the above-described processor.

Here, in the case where the intraoral device according to the present embodiment is used, for example, a specific biting way is judged from a detection value of the pressure sensor, and the device is activated/operated without using the hand.

Further, in the case where the bone-conduction module is provided on the substrate, the intraoral device according to the present embodiment has a bone-conduction function (for example, a function of converting sound indicated by content data into a frequency of vibration and conveying sound by directly transmitting vibration to the inner ear from the bone of the jaw at the frequency of vibration). In the case where the bone-conduction function is implemented, the third party other than the guide target cannot hear the sound, while the guide target can hear the sound indicated by the content data.

The intraoral device according to the present embodiment operates using, for example, power generated using a body temperature (for example, power generated using a thermo-couple structure) and power stored in the power storage module. In the case where the power storage module is detachable from the substrate, it is possible to charge the power storage module in a state where the power storage module is detached.

Because saliva in the oral cavity is secreted from a parotid gland, a submaxillary gland and a sublingual gland, at the intraoral device according to the present embodiment, for example, the enzyme sensor is disposed at a position close to outlets of these glands.

Figure 12:
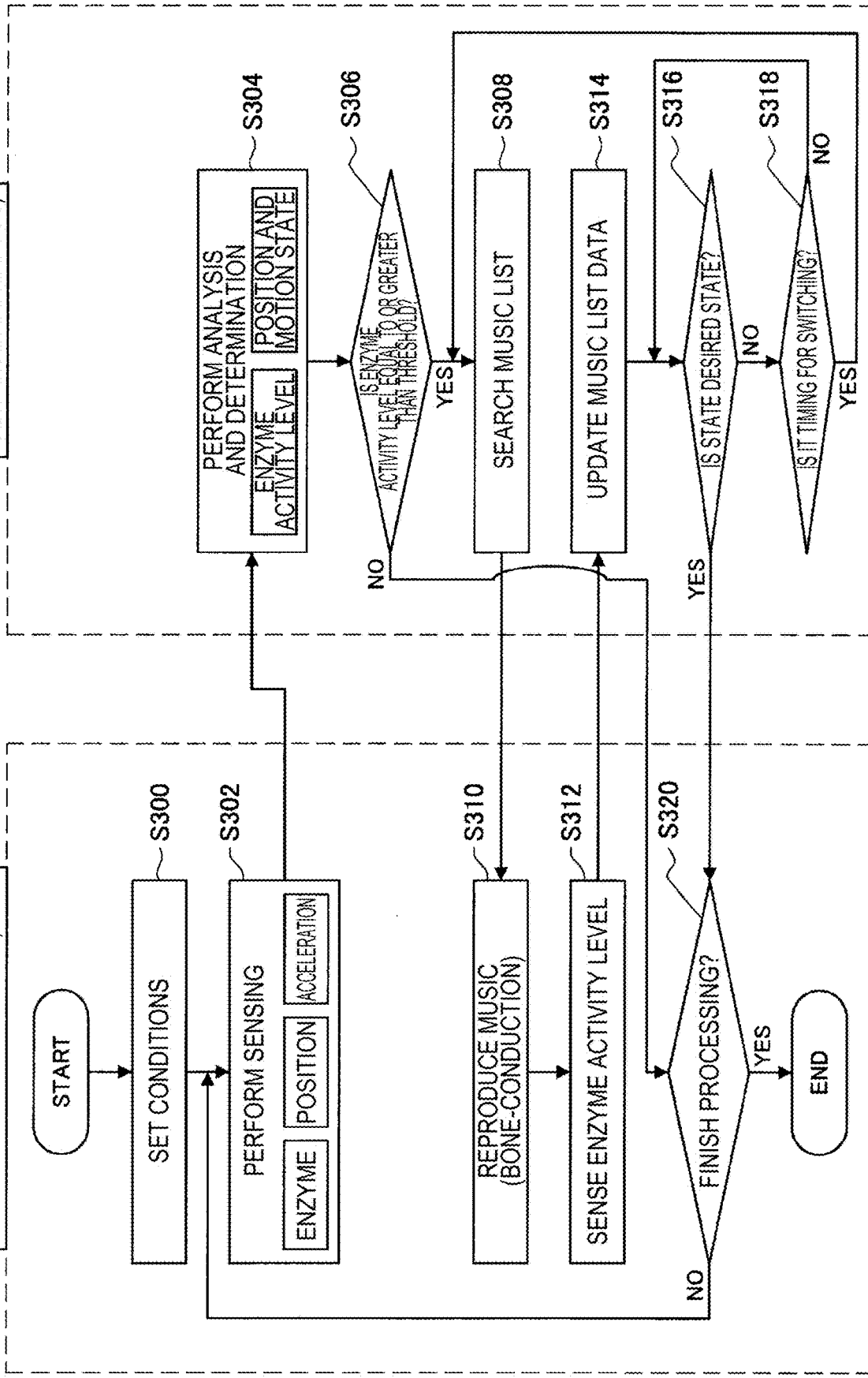
FIG. 12 is a flowchart for explaining an example of processing relating to a first application example of the state control method according to the present embodiment.

FIG. 12 is a flowchart for explaining an example of processing according to the first application example of the state control method according to the present embodiment. FIG. 12 illustrates an example where the apparatus at the guide target side is an "intraoral device", and the state control apparatus according to the present embodiment is a "server".

The apparatus at the guide target side sets conditions as in S100 in FIG. 9 (S300). FIG. 13 is an explanatory diagram illustrating an example of the set conditions according to the present embodiment and illustrates an example of a condition setting screen similar to that in FIG. 2.

The apparatus at the guide target side sequentially detects an enzyme, a position and acceleration using the enzyme sensor, the position sensor, the acceleration sensor, or the like (S302).

The state control apparatus according to the present embodiment, for example, acquires the enzyme activity level S based on the information indicating the detection result of the enzyme as in S104 in FIG. 9 and predicts a current motion state of the guide target based on the information indicating the detection result of the position and the information indicating the detection result of acceleration (S304).

Here, by the current motion state of the guide target being predicted in step S304, in the processing in step S308 which will be described later, for example, it is possible to set content data having a beat per minute (BPM) close to motion pace as the candidate content data. In the case where the state is predicted as a state where the guide target is walking, for example, content data having 120 to 130 [bpm] is set as the candidate content data. Further, in the case where the state is predicted as a state where the guide target is running, for example, content data having 160 to 175 [bpm] is set as the candidate content data.

The state control apparatus according to the present embodiment determines whether or not the enzyme activity level S is equal to or greater than the threshold $S_L$ (S306).

In the case where it is not determined in step S306 that the enzyme activity level S is equal to or greater than the threshold $S_L$, the state control apparatus according to the present embodiment causes the apparatus at the guide target side to perform processing in step S320 which will be described later.

Further, in the case where it is determined in step S306 that the enzyme activity level S is equal to or greater than the threshold $S_L$, the state control apparatus according to the present embodiment, for example, determines the content data to be used for guiding the state of the target feeling of the guide target by searching a music list (an example of the content list) as in S108 in FIG. 9 (S308). Here, in step S308, for example, the search range may be narrowed down by setting a reproduction location close to a surrounding environment of the guide target as the search range using the information indicating the detection result of the position. Further, in step S308, the content data to be used for guiding the state of the target feeling of the guide target is determined using the value according to the set guide conditions (for example, the threshold of the enzyme activity level $S_L=1$ (corresponding to the enzyme activity level which is twice a normal average enzyme activity level), $\Delta S=0.5 \cdot S$, the threshold of the correlation coefficient $R_L=0.5$, the control value $S_a=0.3$ (corresponding to the enzyme activity level which is 1.3 times of the normal average enzyme activity level), and dS/dt is randomly determined using a random number).

The state control apparatus according to the present embodiment causes the apparatus at the guide target side to reproduce the determined content data (an example of processing relating to the feeling guiding medium). The state control apparatus according to the present embodiment, for example, causes the apparatus at the guide target side to reproduce the determined content data by transmitting a command for performing reproduction processing and the determined content data (or information indicating a location where the determined content data is stored) to the apparatus at the guide target side.

The apparatus at the guide target side, for example, reproduces music indicated by the determined content data by utilizing the bone-conduction function (S310). Further, the apparatus at the guide target side senses the enzyme activity level S (S312).

By the music indicated by the content data determined in step S310 being reproduced, the state of the target feeling of the guide target is guided to the predetermined set state. Note that, while FIG. 12 illustrates an example where the content data indicates music, the content data may be sound (such as sound of a stream, wave splash, sound of wind and singing of insects) or voice (such as words of appreciation and words of encouragement).

The state control apparatus according to the present embodiment updates the music list data based on the enzyme activity level S being sensed (S314). The state control apparatus according to the present embodiment, for example, performs processing similar to that in S114 in FIG. 9 in step S314.

The state control apparatus according to the present embodiment determines whether or not the enzyme activity level S is in a desired state as in S116 in FIG. 9 (S316).

In the case where it is not determined in step S316 that the enzyme activity level S is in the desired state, the state control apparatus according to the present embodiment determines whether or not it is a timing for switching as in S118 in FIG. 9 (S318).

In the case where it is not determined in step S318 that it is a timing for switching, the state control apparatus according to the present embodiment, for example, repeats the processing from step S316.

In the case where it is determined in step S318 that it is a timing for switching, the state control apparatus according to the present embodiment, for example, repeats the processing from step S308.

In the case where it is determined in step S316 that the enzyme activity level S is in the desired state, or in the case where it is not determined in step S306 that the enzyme activity level S is equal to or greater than the threshold $S_L$, the state control apparatus according to the present embodiment causes the apparatus at the guide target side to determine whether or not to finish the processing. The state control apparatus according to the present embodiment causes the apparatus at the guide target side to determine whether or not to finish the processing by transmitting a command for performing the processing relating to the above-described determination to the apparatus at the guide target side.

The apparatus at the guide target side determines whether or not to finish the processing as in S120 in FIG. 9 (S320).

In the case where it is not determined to finish the processing in step S320, the apparatus at the guide target side, for example, repeats the processing from step S302. Further, in the case where it is not determined to finish the processing in step S320, the apparatus at the guide target side finishes the processing illustrated in FIG. 12.

The state control apparatus according to the present embodiment and the apparatus at the guide target side, for example, perform the processing illustrated in FIG. 12 as the processing according to the first application example of the state control apparatus according to the present embodiment.

Note that the example of the processing according to the first application example of the state control apparatus according to the present embodiment is not limited to the example illustrated in FIG. 12.

Figure 14:
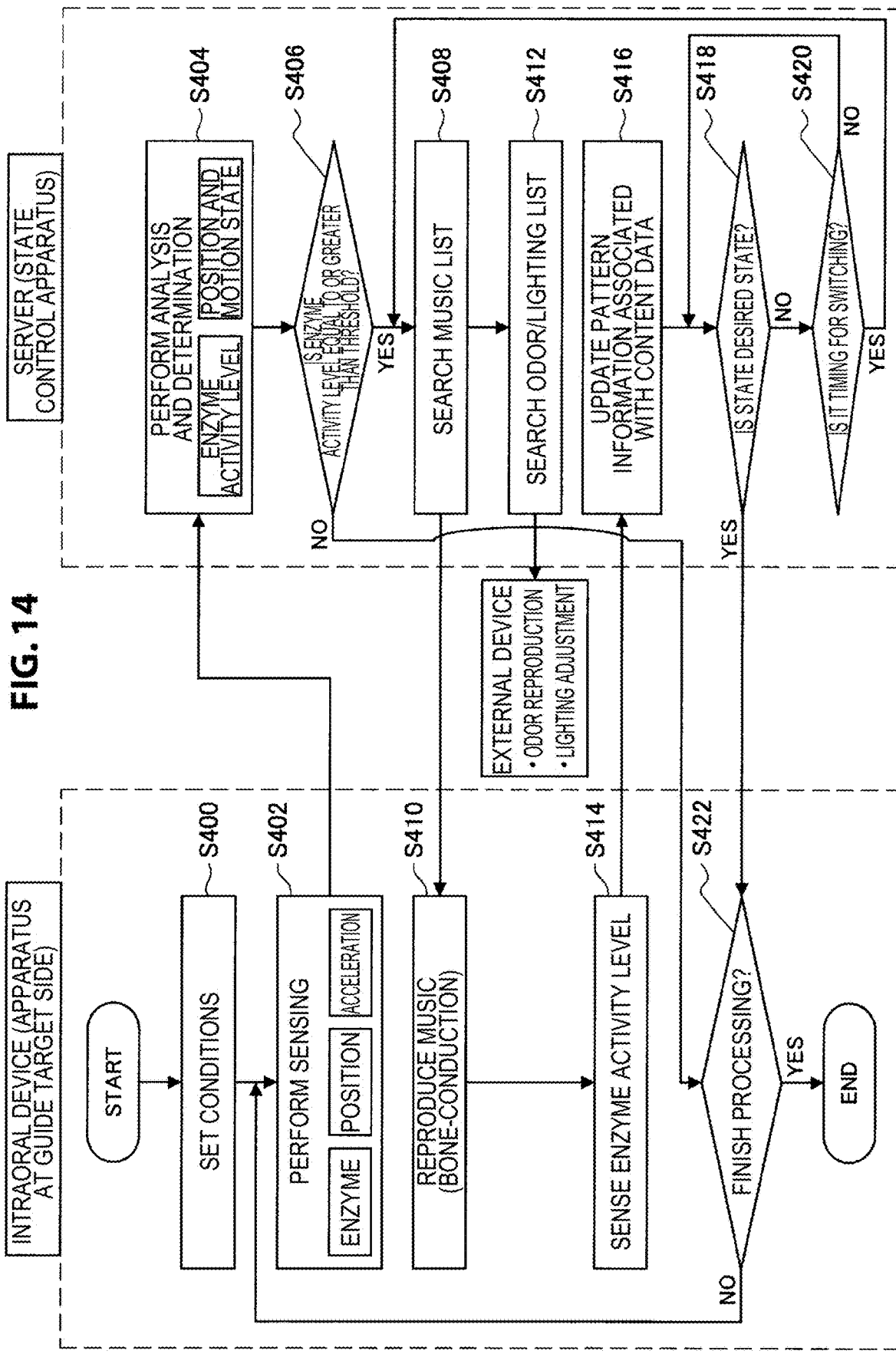
FIG. 14 is a flowchart for explaining another example of the processing relating to the first application example of the state control method according to the present embodiment.

FIG. 14 is a flowchart for explaining another example of the processing according to the first application example of the state control method according to the present embodiment. FIG. 14 illustrates an example where the state control apparatus according to the present embodiment is a "server".

In the processing illustrated in FIG. 14, while the state control apparatus according to the present embodiment and the apparatus at the guide target side perform processing similar to the processing illustrated in FIG. 12, the processing illustrated in FIG. 14 differs from the processing illustrated in FIG. 12 in that, in the case where it is determined in step S406 that the enzyme activity level S is equal to or greater than the threshold $S_L$, the state control apparatus according to the present embodiment further performs processing in step S412.

Specifically, the state control apparatus according to the present embodiment, for example, searches an odor list (an example of the content list) and a lighting list (an example of the content list) to determine odor output control data (an example of the feeling guiding medium) and lighting adjustment control data (an example of the feeling guiding medium) to be used for guiding the state of the target feeling of the guide target by performing processing similar to the processing in S108 in FIG. 9 in step S412. The state control apparatus according to the present embodiment then, for example, causes an external device to output an odor according to the odor output control data and adjust lighting according to the lighting adjustment control data by transmitting the determined odor output control data and lighting adjustment control data to the external device (an example of the processing relating to the feeling guiding medium).

For example, by the processing in step S412 in FIG. 14 being performed, it is possible to guide the state of the feeling (reduce stress) to a state of feeling to which an effect of an odor and a lighting effect, as well as music, are added.

Note that it goes without saying that an effect for further reducing stress is not limited to the effect of the odor and the lighting effect.

[4-2] Second Application Example: Stress Reduction Using Image and Text

As a second application example, an application example relating to stress reduction using an image and text will be described. The second application example is implemented with the state control system having the apparatus at the guide target side and the state control apparatus according to the present embodiment. Note that the second application example can be also implemented in the case where the apparatus at the guide target side plays a role of the state control apparatus according to the present embodiment. In the following description, a case will be described as an example where the second application example is implemented with the state control system.

Figure 15:
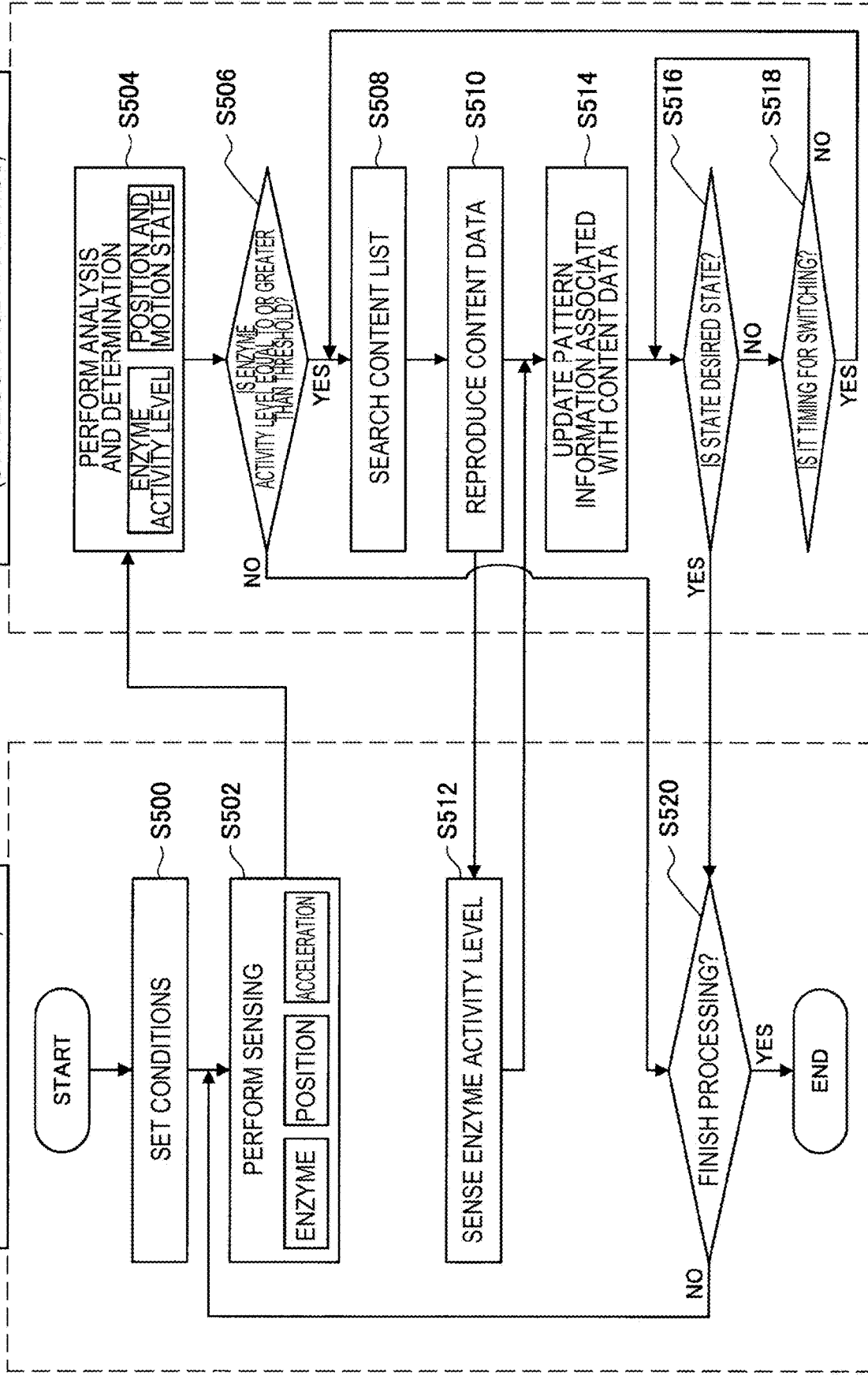
FIG. 15 is a flowchart for explaining an example of processing relating to a second application example of the state control method according to the present embodiment.

FIG. 15 is a flowchart for explaining an example of processing according to the second application example of the state control method according to the present embodiment. FIG. 15 illustrates an example where the apparatus at the guide target side is an "intraoral device", and the state control apparatus according to the present embodiment is a "device with display function" including a display unit (which will be described later).

The apparatus at the guide target side sets conditions as in S300 in FIG. 12 (S500).

The apparatus at the guide target side sequentially detects an enzyme, a position and acceleration using the enzyme sensor, the position sensor, the acceleration sensor, or the like, as in S302 in FIG. 12 (S502).

The state control apparatus according to the present embodiment, for example, acquires the enzyme activity level S and predicts a current motion state of the guide target as in S304 in FIG. 12. (S504).

The state control apparatus according to the present embodiment determines whether or not the enzyme activity level S is equal to or greater than the threshold $S_L$ (S506).

In the case where it is not determined in step S506 that the enzyme activity level S is equal to or greater than the threshold $S_L$, the state control apparatus according to the present embodiment causes the apparatus at the guide target side to perform processing of step S520 which will be described later.

Further, in the case where it is determined in step S506 that the enzyme activity level S is equal to or greater than the threshold $S_L$, the state control apparatus according to the present embodiment, for example, searches the content list to determine the content data to be used for guiding the state of the target feeling of the guide target as in S308 in FIG. 12 (S508). Here, examples of the content data determined in step S508 include, for example, data indicating an image or text.

The state control apparatus according to the present embodiment then reproduces the determined content data and displays an image or text indicated by the content data on a display screen of the display unit (which will be described later) or a display screen of an external display device (S510. An example of processing relating to the feeling guiding medium). By the state control apparatus according to the present embodiment reproducing the content data determined in step S510, the state of the target feeling of the guide target is guided to the predetermined set state with the image or text displayed on the display screen.

The apparatus at the guide target side senses the enzyme activity level S (S512).

The state control apparatus according to the present embodiment, for example, updates the pattern information associated with the reproduced content data based on the enzyme activity level S being sensed as in S114 in FIG. 9 (S514).

The state control apparatus according to the present embodiment determines whether or not the enzyme activity level S is in a desired state as in S316 in FIG. 12 (S516).

In the case where it is not determined in step S516 that the enzyme activity level S is in the desired state, the state control apparatus according to the present embodiment determines whether or not it is a timing for switching as in S318 in FIG. 12 (S518).

In the case where it is not determined in step S518 that it is a timing for switching, the state control apparatus according to the present embodiment, for example, repeats the processing from step S516.

In the case where it is determined in step S518 that it is a timing for switching, the state control apparatus according to the present embodiment, for example, repeats the processing from step S508.

In the case where it is determined in step S516 that the enzyme activity level S is in the desired state or in the case where it is not determined in step S506 that the enzyme activity level S is equal to or greater than the threshold $S_L$, the state control apparatus according to the present embodiment causes the apparatus at the guide target side to determine whether or not to finish the processing.

The apparatus at the guide target side determines whether or not to finish the processing as in S320 in FIG. 12 (S520).

In the case where it is not determined in step S520 to finish the processing, the apparatus at the guide target side, for example, repeats the processing from step S502. Further, in the case where it is determined in step S520 to finish the processing, the apparatus at the guide target side finishes the processing illustrated in FIG. 15.

The state control apparatus according to the present embodiment and the apparatus at the guide target side, for example, perform the processing illustrated in FIG. 15 as the processing according to the second application example of the state control method according to the present embodiment. Note that it goes without saying that the example of the processing according to the second application example of the state control method according to the present embodiment is not limited to the example illustrated in FIG. 15.

[4-3] Third Application Example: Change of Program (for Example, Change of Difficulty Level or Scene of Game)

As a third application example, a first application example relating to change of a program will be described. The third application example is implemented with the state control system including the apparatus at the guide target side and the state control apparatus according to the present embodiment. Note that the third application example can be also implemented in the case where the apparatus at the guide target side plays a role of the state control apparatus according to the present embodiment. In the following description, a case will be described as an example where the third application example is implemented with the state control system.

Figure 16:
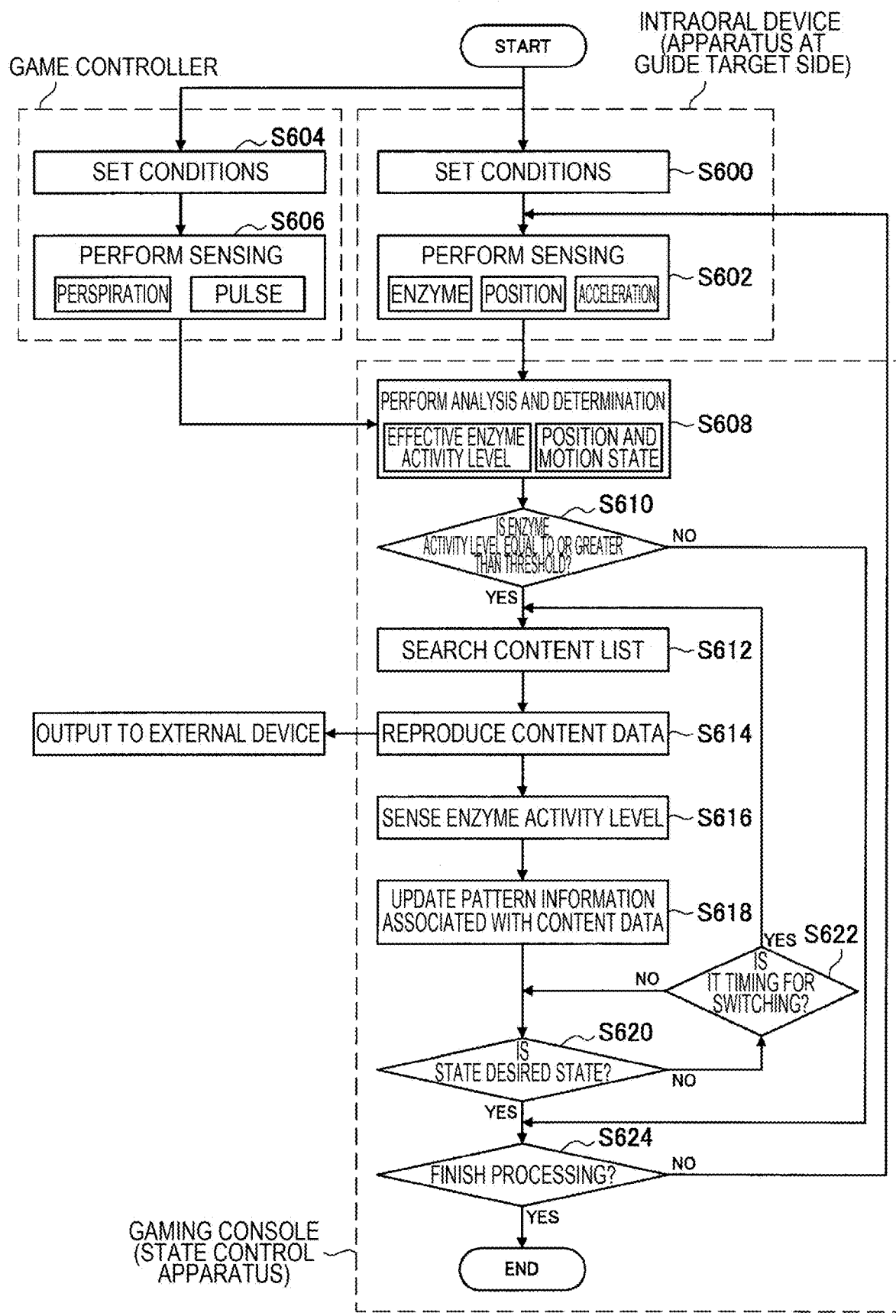
FIG. 16 is a flowchart for explaining an example of processing relating to a third application example of the state control method according to the present embodiment.

FIG. 16 is a flowchart for explaining an example of processing according to the third application example of the state control method according to the present embodiment.

FIG. 16 illustrates an example where the apparatus at the guide target side is an "intraoral device" and the state control apparatus according to the present embodiment is a "gaming console". Further, FIG. 16 illustrates an example where the state control system further includes a game controller having a function of detecting perspiration on a body surface (such as, for example, the hand) and a pulse of the guide target. Note that the state control system according to the third application example does not have to include the game controller illustrated in FIG. 16.

Figure 17:
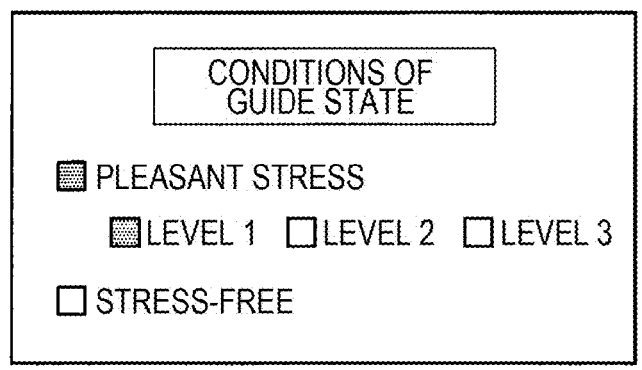
FIG. 17 is an explanatory diagram illustrating an example of set conditions according to the present embodiment.

The apparatus at the guide target side sets conditions as in S300 in FIG. 12 (S600). FIG. 17 is an explanatory diagram illustrating an example of the set conditions according to the present embodiment and illustrates an example of the condition setting screen.

The apparatus at the guide target side sequentially detects an enzyme, a position and acceleration using the enzyme sensor, the position sensor, the acceleration sensor, or the like, as in S302 in FIG. 12 (S602).

The game controller sets conditions as in S300 in FIG. 12 (S604).

The game controller detects an amount of perspiration, a pulse, or the like, using various kinds of sensors of the game controller (S606).

The state control apparatus according to the present embodiment, for example, acquires an effective enzyme activity level S' and predicts a current motion state of the guide target as in S504 in FIG. 12 (S608).

Here, the state control apparatus according to the present embodiment, for example, acquires the enzyme activity level S as in S504 in FIG. 12. Further, the state control apparatus according to the present embodiment acquires an effective enzyme activity level S' by performing calculation of the following equation 2 using the enzyme activity level S, information indicating the amount of perspiration detected in step S606 (an example of the biological information) and information indicating the pulse detected in step S606 (an example of the biological information). The following equation 2 is an equation for calculating the enzyme activity level while taking into account an effect of an "amount of perspiration P normalized with a normal value based on the information indicating the amount of perspiration detected in step S606" and a "pulse B normalized with a normal value based on the information indicating the pulse detected in step S606".

Further, "$\beta_S$", "$\beta_P$" and "$\beta_B$" indicated in the following equation 2 are weighting parameters, and the values of "$\beta_S$", "$\beta_P$" and "$\beta_B$" change depending on which detection result of the enzyme, the perspiration and the pulse, weight is placed on. Note that, for example, as long as each detection result of the enzyme, the perspiration and the pulse is taken into account, a method for calculating the effective enzyme activity level S' is not limited to the following equation 2.

[Math. 1]

$$S' = \sqrt{\frac{\beta_S \cdot S^2 + \beta_P \cdot S^2 + \beta_B \cdot S^2}{\beta_S + \beta_P + \beta_B}} \quad \text{(equation 2)}$$

The state control apparatus according to the present embodiment determines whether or not the effective enzyme activity level S' is equal to or greater than the threshold $S_L$ (S610).

In the case where it is not determined in step S610 that the enzyme activity level S is equal to or greater than the threshold $S_L$, the state control apparatus according to the present embodiment performs processing in step S624 which will be described later.

Further, in the case where it is determined in step S610 that the effective enzyme activity level S' is equal to or greater than the threshold $S_L$, the state control apparatus according to the present embodiment, for example, searches the content list to determine the content data to be used for guiding the state of the target feeling of the guide target as in S308 in FIG. 12 (S612).

Here, examples of the content data determined in step S612 include, for example, a program relating to change of a difficulty level or a scene of a game. In the following description, a case will be described as an example where the content data determined in step S612 is a program relating to change of a scene of a game. FIG. 18 is an explanatory diagram illustrating an example of a content list according to the present embodiment.

The state control apparatus according to the present embodiment then reproduces the determined content data and displays an image, or the like, according to the scene corresponding to the reproduction result of the content data on a display screen, or the like, of the display unit (which will be described later) (S614. An example of the processing relating to the feeling guiding medium).

Figure 19:
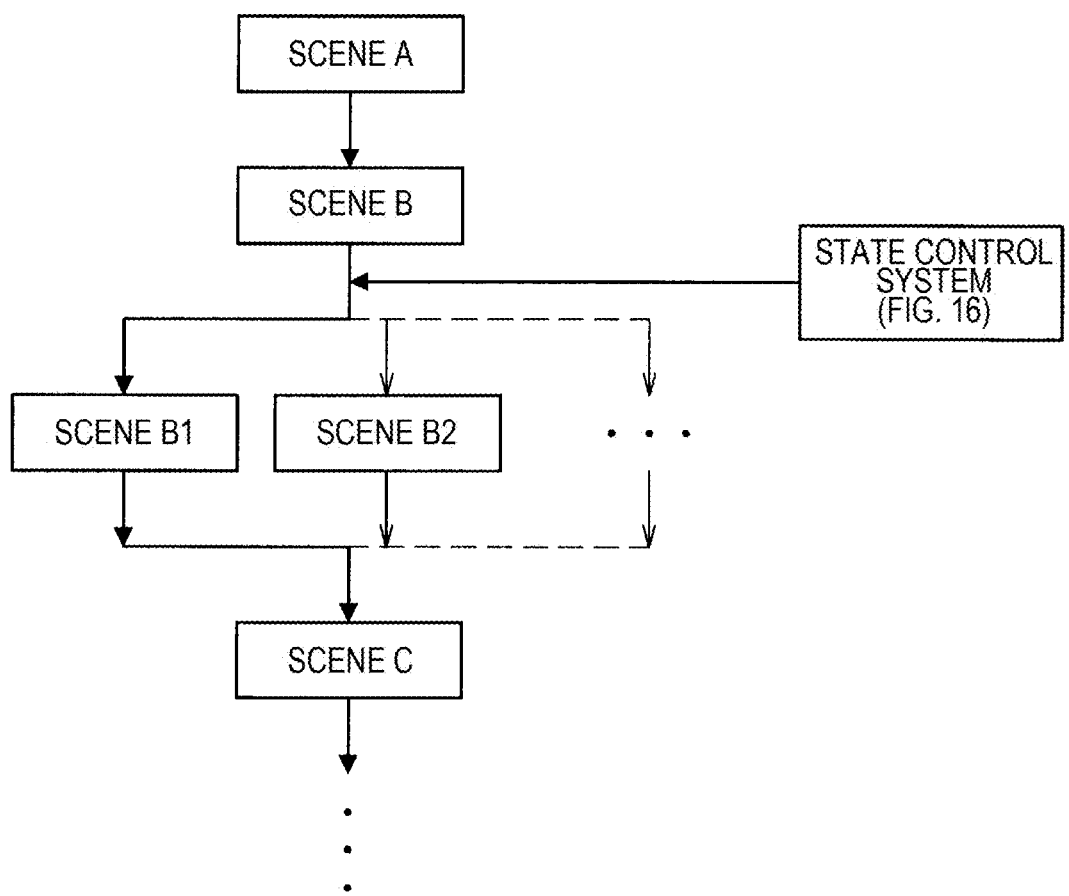
FIG. 19 is an explanatory diagram for explaining processing relating to the third application example of the state control method according to the present embodiment.

FIG. 19 is an explanatory diagram for explaining processing according to the third application example of the state control method according to the present embodiment and illustrates concept of the change of the scene of the game by the processing in step S614 at the state control apparatus according to the present embodiment.

By the state control apparatus according to the present embodiment reproducing the content data determined in step S614, the scene is switched as illustrated in FIG. 19 according to the state of the target feeling of the guide target. Therefore, by the state control apparatus according to the present embodiment reproducing the content data determined in step S614, the state of the target feeling of the guide target is guided to the predetermined set state.

The state control apparatus according to the present embodiment senses the enzyme activity level S as in step S112 in FIG. 9 (S616).

The state control apparatus according to the present embodiment, for example, updates the pattern information associated with the reproduced content data based on the enzyme activity level S being sensed as in S114 in FIG. 9 (S618). Further, the state control apparatus according to the present embodiment may, for example, update the pattern information associated with the reproduced content data based on the calculated effective enzyme activity level S' in step S618.

The state control apparatus according to the present embodiment determines whether or not the enzyme activity level S is in a desired state as in S316 in FIG. 12 (S620). Further, the state control apparatus according to the present embodiment may, for example, determine whether or not the calculated effective enzyme activity level S' is in a desired state in step S618.

In the case where it is not determined in step S620 that the enzyme activity level S is in the desired state, the state control apparatus according to the present embodiment determines whether or not it is a timing for switching as in S318 in FIG. 12 (S622).

In the case where it is not determined in step S622 that it is a timing for switching, the state control apparatus according to the present embodiment, for example, repeats the processing from step S620.

In the case where it is determined in step S622 that it is a timing for switching, the state control apparatus according to the present embodiment, for example, repeats the processing from step S612.

In the case where it is determined in step S620 that the enzyme activity level S is in the desired state or in the case where it is determined in step S610 that the enzyme activity level S is equal to or greater than the threshold $S_L$, the state control apparatus according to the present embodiment determines whether or not to finish the processing as in step S120 in FIG. 9 (S624).

In the case where it is not determined in step S624 to finish the processing, the state control apparatus according to the present embodiment, for example, causes the apparatus at the guide target side to perform processing from step S602. Further, in the case where it is determined in step S624 to finish the processing, the state control apparatus according to the present embodiment finishes the processing illustrated in FIG. 16.

The state control apparatus according to the present embodiment and the apparatus at the guide target side, for example, perform the processing illustrated in FIG. 16 as the processing according to the third application example of the state control method according to the present embodiment. Here, in the case where the processing illustrated in FIG. 16 is performed, for example, because it becomes possible to provide a game scene suited to a user according to the state of the user who is the guide target, it is possible to efficiently sustain a level of excitement and satisfaction of the user for the game.

Note that the example of the processing according to the third application example of the state control method according to the present embodiment is not limited to the example illustrated in FIG. 16.

For example, the state control apparatus according to the present embodiment can change the difficulty level of the game according to the state of the user who is the guide target by changing the program. Also in the case where the difficulty level of the game is changed, it is possible to efficiently sustain the level of excitement and satisfaction of the user for the game.

Further, the processing according to the third application example of the state control method according to the present embodiment can be applied to an attraction, or the like, of an amusement park by, for example, replacing the game console illustrated in FIG. 16 with an attraction apparatus or by replacing the game console illustrated in FIG. 16 with an item used for an attraction.

4-4. Fourth Application Example: Change of Program (for Example, Change of Security Lock Level)

As a fourth application example, a second application example relating to change of the program will be described. The fourth application example is implemented with the state control system including the apparatus at the guide target side and the state control apparatus according to the present embodiment. Note that the fourth application example can be implemented also in the case where the apparatus at the guide target side plays a role of the state control apparatus according to the present embodiment. In the following description, a case will be described as an example where the fourth application example is implemented with the state control system.

Figure 20:
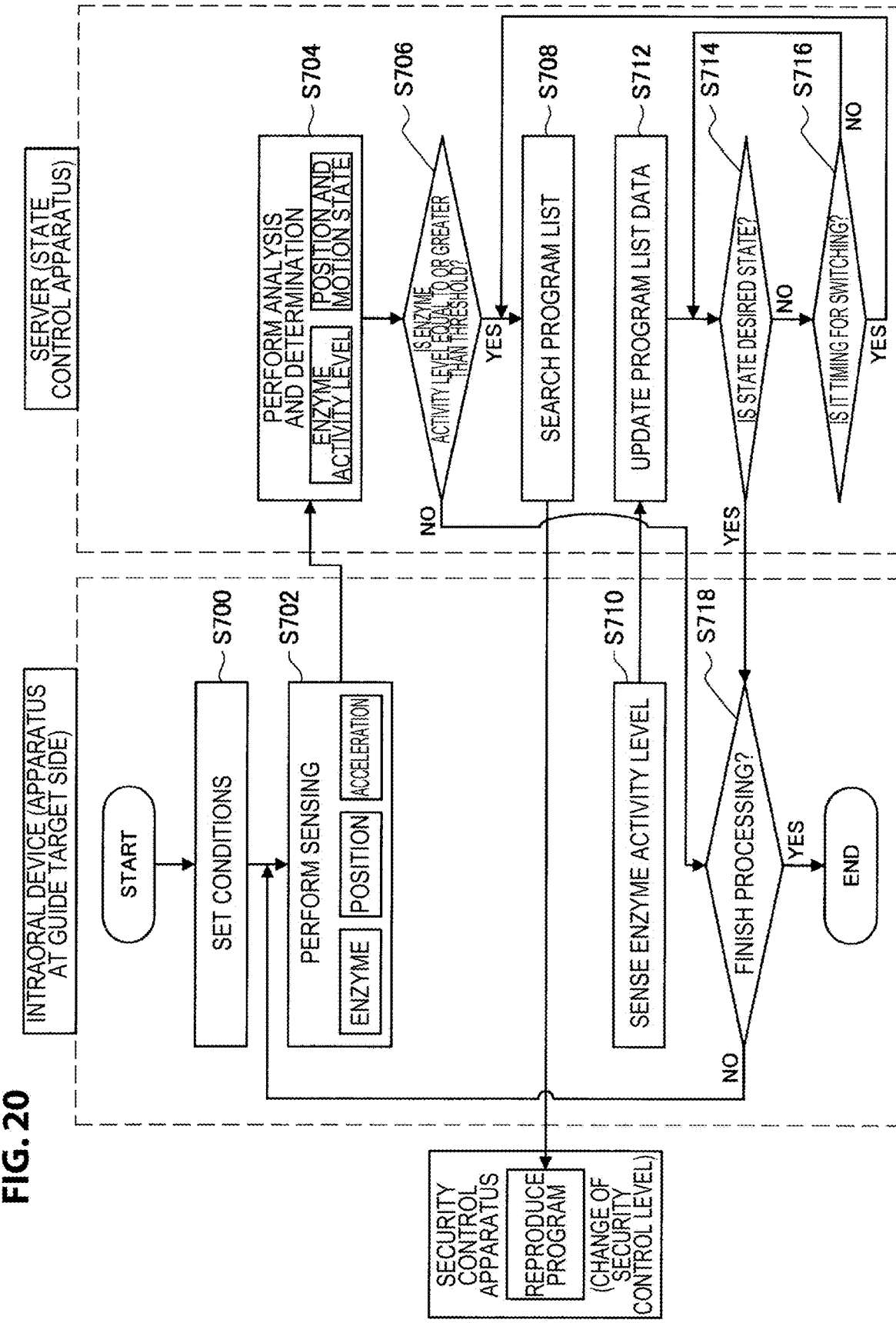
FIG. 20 is a flowchart for explaining an example of processing relating to a fourth application example of the state control method according to the present embodiment.

FIG. 20 is a flowchart for explaining an example of processing according to the fourth application example of the state control method according to the present embodiment. FIG. 20 illustrates an example where the apparatus at the guide target side is an "intraoral device" and the state control apparatus according to the present embodiment is a "server".

The apparatus at the guide target side sets conditions as in S300 in FIG. 12 (S700).

The apparatus at the guide target side sequentially detects an enzyme, a position and acceleration using the enzyme sensor, the position sensor, the acceleration sensor, or the like, as in S302 in FIG. 12 (S702).

The state control apparatus according to the present embodiment, for example, acquires the enzyme activity level S and predicts a current motion state of the guide target as in S304 in FIG. 12 (S704).

The state control apparatus according to the present embodiment determines whether or not the enzyme activity level S is equal to or greater than the threshold $S_L$ (S706).

In the case where it is not determined in step S706 that the enzyme activity level S is equal to or greater than the threshold $S_L$, the state control apparatus according to the present embodiment causes the apparatus at the guide target side to perform processing in step S718 which will be described later.

Further, in the case where it is determined in step S706 that the enzyme activity level S is equal to or greater than the threshold $S_L$, the state control apparatus according to the present embodiment, for example, searches the program list to determine a program to be used for guiding the state of the target feeling of the guide target as in S308 in FIG. 12 (S708). Here, examples of the program determined in step S708 include, for example, a program for setting a security lock level of electronic equipment (such as, for example, factory equipment, a vehicle and medical equipment).

The state control apparatus according to the present embodiment then causes an external security control apparatus to execute the determined program (an example of the processing relating to the feeling guiding medium). The state control apparatus according to the present embodiment, for example, causes the security control apparatus to execute the determined program by transmitting a command for executing the program and the determined program (or information indicating a location where the determined program is stored) to the security control apparatus.

By the state control apparatus according to the present embodiment causing the security control apparatus to execute the determined program, it is possible to change a lock level of the security control apparatus according to the state of the target feeling of the guide target. Therefore, by the state control apparatus according to the present embodiment causing the security control apparatus to execute the determined program, for example, it is possible to suppress erroneous operation of the equipment caused by feeling of "displeasure" of the user who is the guide target.

The apparatus at the guide target side senses the enzyme activity level S (S710).

The state control apparatus according to the present embodiment updates the program list data (S712). The state control apparatus according to the present embodiment, for example, updates the pattern information associated with the executed program based on the enzyme activity level S being sensed as in S114 in FIG. 9.

The state control apparatus according to the present embodiment determines whether or not the enzyme activity level S is in a desired state as in S316 in FIG. 12 (S714).

In the case where it is not determined in step S714 that the enzyme activity level S is in the desired state, the state control apparatus according to the present embodiment determines whether or not it is a timing for switching as in S318 in FIG. 12 (S716).

In the case where it is not determined in step S716 that it is a timing for switching, the state control apparatus according to the present embodiment, for example, repeats the processing from step S714.

In the case where it is determined in step S716 that it is a timing for switching, the state control apparatus according to the present embodiment, for example, repeats the processing from step S708.

In the case where it is determined in step S714 that the enzyme activity level S is in the desired state, or in the case where it is not determined in step S706 that the enzyme activity level S is equal to or greater than the threshold $S_L$, the state control apparatus according to the present embodiment causes the apparatus at the guide target side to determine whether or not to finish the processing.

The apparatus at the guide target side determines whether or not to finish the processing as in S320 in FIG. 12 (S718).

In the case where it is not determined in step S718 to finish the processing, the apparatus at the guide target side, for example, repeats the processing from step S702. Further, in the case where it is determined in step S718 to finish the processing, the apparatus at the guide target side finishes the processing illustrated in FIG. 20.

The state control apparatus according to the present embodiment and the apparatus at the guide target side, for example, perform the processing illustrated in FIG. 20 as the processing according to the fourth application example of the state control apparatus according to the present embodiment.

Note that the example of the processing according to the fourth application example of the state control method according to the present embodiment is not limited to the example illustrated in FIG. 20.

For example, in the case where the program determined by the state control apparatus according to the present embodiment in step S708 is a control program for a robot (such as, for example, a nursing-care robot and a watching robot), it is possible to realize a robot which can perform action, gesture and sound output close to sense of the human which reflects feeling of "pleasure" and "displeasure" of the user who is the guide target.

[4-5] Fifth Application Example: Notification of State of Target Feeling of Guide Target As a fifth application example, an application example relating to notification of the state of the target feeling of the guide target will be described. The fifth application example is implemented with the state control system including the apparatus at the guide target side and the state control apparatus according to the present embodiment. Note that the fifth application example can be also implemented in the case where the apparatus at the guide target side plays a role of the state control apparatus according to the present embodiment. In the following description, a case will be described as an example where the fifth application example is implemented with the state control system.

Figure 21:
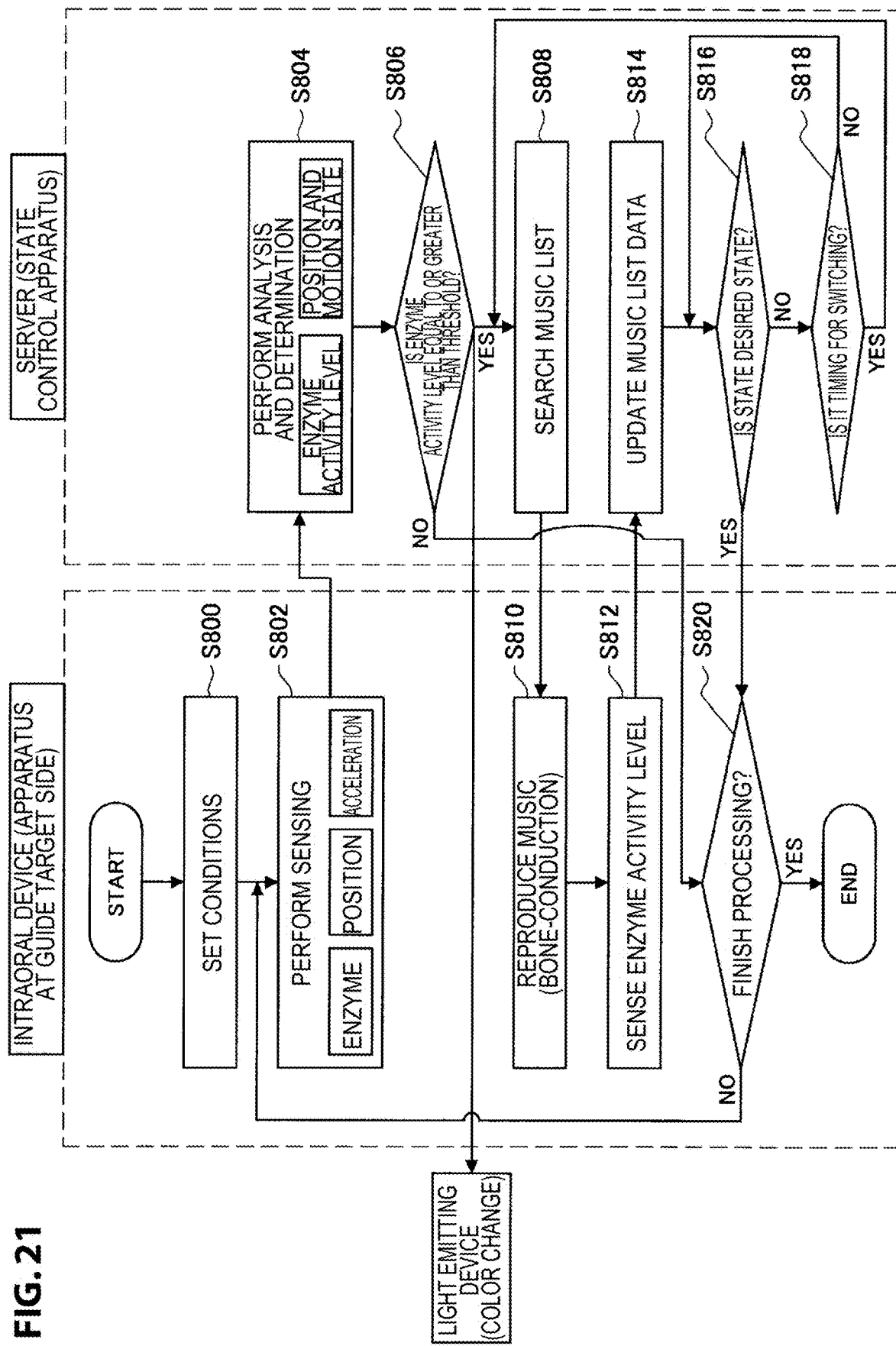
FIG. 21 is a flowchart for explaining an example of processing relating to a fifth application example of the state control method according to the present embodiment.

FIG. 21 is a flowchart for explaining an example of processing according to the fifth application example of the state control method according to the present embodiment. FIG. 21 illustrates an example where the apparatus at the guide target side is an "intraoral device" and the state control apparatus according to the present embodiment is a "server".

The apparatus at the guide target side sets conditions as in S300 in FIG. 12 (S800).

The apparatus at the guide target side sequentially detects an enzyme, a position and acceleration using the enzyme sensor, the position sensor, the acceleration sensor, or the like, as in S302 in FIG. 12 (S802).

The state control apparatus according to the present embodiment, for example, acquires the enzyme activity level S and predicts a current motion state of the guide target as in S304 in FIG. 12 (S804).

The state control apparatus according to the present embodiment determines whether or not the enzyme activity level S is equal to or greater than the threshold $S_L$ (S806).

In the case where it is not determined in step S806 that the enzyme activity level S is equal to or greater than the threshold $S_L$, the state control apparatus according to the present embodiment causes the apparatus at the guide target side to perform processing in step S820 which will be described later.

Further, in the case where it is determined in step S806 that the enzyme activity level S is equal to or greater than the threshold $S_L$, the state control apparatus according to the present embodiment, for example, searches the music list to determine the content data to be used for guiding the state of the target feeling of the guide target as in S308 in FIG. 12 (S808). Here, the content data determined in step S808 is, for example, data indicating music.

The state control apparatus according to the present embodiment then causes the apparatus at the guide target side to reproduce the determined content data (an example of the processing relating to the feeling guiding medium). By the state control apparatus according to the present embodiment reproducing the content data determined in step S808, the state of the target feeling of the guide target is guided to the predetermined set state by the music indicated by the reproduced content data.

Further, in the case where it is determined in step S806 that the enzyme activity level S is equal to or greater than the threshold $S_L$, the state control apparatus according to the present embodiment, for example, causes the light emitting device to emit light of color according to the value of the enzyme activity level S. The state control apparatus according to the present embodiment, for example, causes the light emitting device (or an apparatus including the light emitting device) to emit light of color according to the value of the enzyme activity level S by transmitting a command for emitting light of color according to the value of the enzyme activity level S to the light emitting device.

The light emitting device according to the fifth application example is, for example, provided at an arbitrary apparatus such as a ring-type apparatus, a necklace type apparatus, a collar type apparatus, a spectacle type apparatus and a pierce type apparatus, which can be worn by the guide target. Further, the light emitting device is not limited to one provided at the apparatus which can be worn by the guide target, and may be provided at an arbitrary apparatus which allows the third party other than the guide target to recognize light emitted by the light emitting device in association with the guide target.

Note that, while not illustrated in FIG. 21, the state control apparatus according to the present embodiment, for example, performs processing relating to control of light emission of the light emitting device from when it is determined in step S806 that the enzyme activity level S is equal to or greater than the threshold $S_L$ until the processing is finished in step S820 which will be described later.

The apparatus at the guide target side, for example, reproduces music indicated by the content data determined by utilizing the bone-conduction function (S810). Further, the apparatus at the guide target side senses the enzyme activity level S (S812).

The state control apparatus according to the present embodiment, for example, updates the music list data based on the enzyme activity level S being sensed as in S314 in FIG. 12 (S814).

The state control apparatus according to the present embodiment determines whether or not the enzyme activity level S is in a desired state as in S316 in FIG. 12 (S816).

In the case where it is not determined in step S816 that the enzyme activity level S is in the desired state, the state control apparatus according to the present embodiment determines whether or not it is a timing for switching as in S318 in FIG. 12 (S818).

In the case where it is not determined in step S818 that it is a timing for switching, the state control apparatus according to the present embodiment, for example, repeats the processing from step S816.

In the case where it is determined in step S818 that it is a timing for switching, the state control apparatus according to the present embodiment, for example, repeats the processing from step S808.

In the case where it is determined in step S816 that the enzyme activity level S is in the desired state, or in the case where it is not determined in step S806 that the enzyme activity level S is equal to or greater than the threshold $S_L$, the state control apparatus according to the present embodiment causes the apparatus at the guide target side to determine whether or not to finish the processing.

The apparatus at the guide target side determines whether or not to finish the processing as in S320 in FIG. 12 (S820).

In the case where it is not determined in step S820 to finish the processing, the apparatus at the guide target side, for example, repeats the processing from step S802. Further, in the case where it is determined in step S820 to finish the processing, the apparatus at the guide target side finishes the processing illustrated in FIG. 21.

The state control apparatus according to the present embodiment and the apparatus at the guide target side, for example, perform the processing illustrated in FIG. 21 as the processing according to the fifth application example of the state control method according to the present embodiment. By the processing illustrated in FIG. 21 being performed, it is possible to notify the third party other than the guide target of the state of the target feeling of the guide target as well as guide the target feeling of the guide target to the predetermined state. Therefore, by the processing according to the fifth application example of the state control method according to the present embodiment being performed, even in the case where the guide target is, for example, a disabled person, a patient, a pet, or the like, who have difficulty in conveying feeling of "pleasure", "displeasure", or the like, by words, it is possible to convey the state of the feeling of the guide target to the surrounding third party.

Note that it goes without saying that the example of the processing according to the fifth application example of the state control method according to the present embodiment is not limited to the example illustrated in FIG. 21.

4-6. Sixth Application Example: Change of Program (for Example, Variable Display on Display Screen of Display Apparatus Provided in Front of Store)

As a fourth application example, a third application example relating to change of the program will be described.

The sixth application example is implemented with the state control system including the apparatus at the guide target side and the state control apparatus according to the present embodiment. Note that the sixth application example can be also implemented in the case where the apparatus at the guide target side plays a role of the state control apparatus according to the present embodiment. In the following description, a case will be described as an example where the sixth application example is implemented with the state control system.

Figure 22:
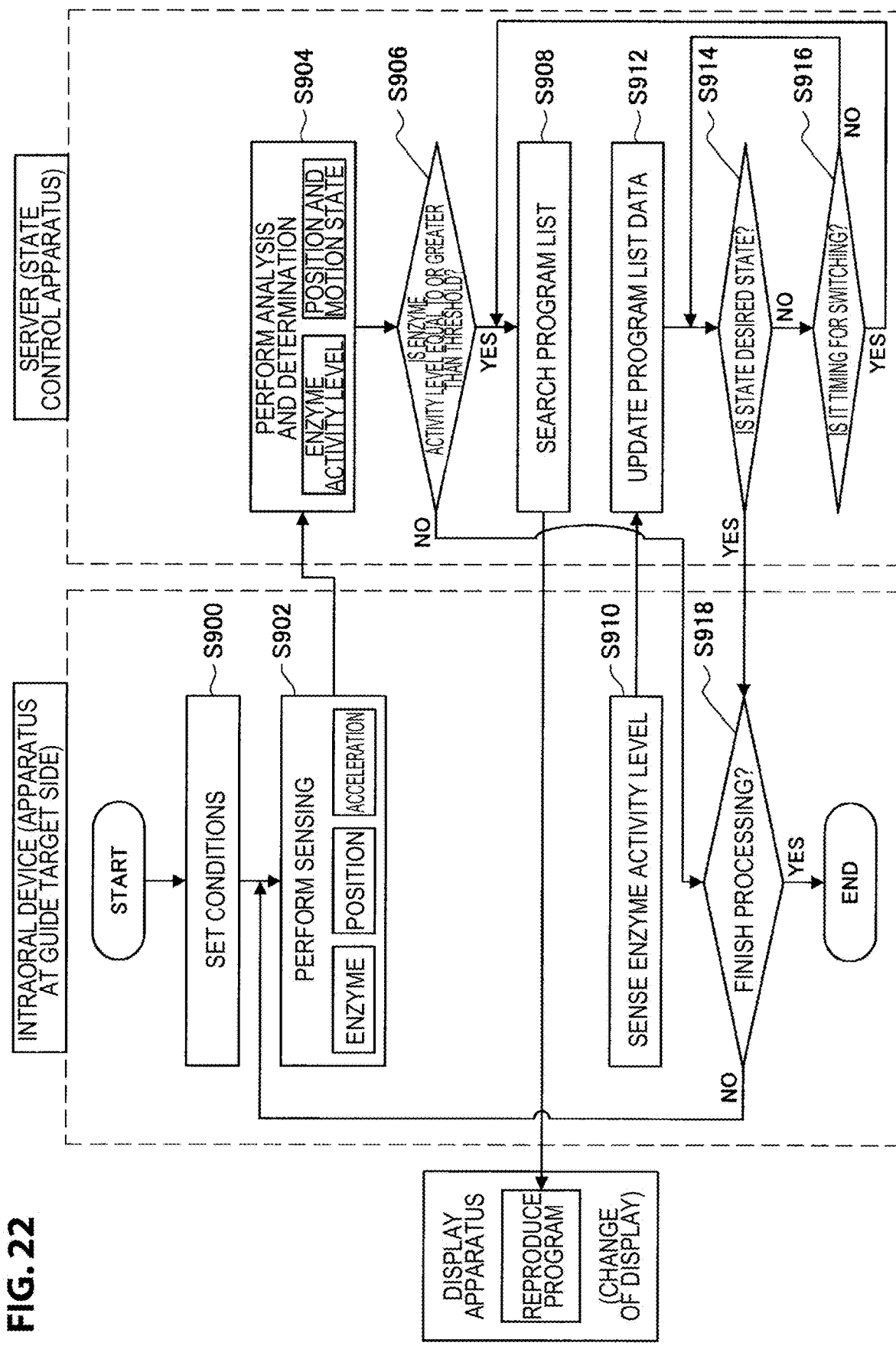
FIG. 22 is a flowchart for explaining an example of processing relating to a sixth application example of the state control method according to the present embodiment.

FIG. 22 is a flowchart for explaining an example of processing according to the sixth application example of the state control method according to the present embodiment. FIG. 22 illustrates an example where the apparatus at the guide target side is an "intraoral device" and the state control apparatus according to the present embodiment is a "server".

The apparatus at the guide target side sets condition as in S300 in FIG. 12 (S900).

The apparatus at the guide target side sequentially detects an enzyme, a position and acceleration using the enzyme sensor, the position sensor, the acceleration sensor, or the like, as in S302 in FIG. 12 (S902).

The state control apparatus according to the present embodiment, for example, acquires the enzyme activity level S and predicts a current motion state of the guide target as in S304 in FIG. 12 (S904).

The state control apparatus according to the present embodiment determines whether or not the enzyme activity level S is equal to or greater than the threshold $S_L$ (S906).

In the case where it is not determined in step S906 that the enzyme activity level S is equal to or greater than the threshold $S_L$, the state control apparatus according to the present embodiment causes the apparatus at the guide target side to perform processing in step S918 which will be described later.

Further, in the case where it is determined in step S906 that the enzyme activity level S is equal to or greater than the threshold $S_L$, the state control apparatus according to the present embodiment, for example, searches the program list to determine the program to be used for guiding the state of the target feeling of the guide target as in S308 in FIG. 12 (S908). Here, examples of the program determined in step S908 include, for example, a program for displaying an image, or the like, which introduces goods and service.

Here, in the case where there are a plurality of guide targets, the state control apparatus according to the present embodiment can, for example, determine the program to be used for guiding the state of the target feeling of the guide target while taking into account the enzyme activity levels S of the respective guide targets. In the case where the enzyme activity levels S of the plurality of guide targets are taken into account, the state control apparatus according to the present embodiment, for example, calculates an average value of the enzyme activity levels S of the plurality of guide targets whose enzyme activity level S is equal to or greater than the threshold $S_L$ and determines the program to be used for guiding the state of the target feeling of the guide target using a pattern of temporal change of the average value of the enzyme activity levels S. Note that it goes without saying that the processing in the case where the enzyme activity levels S of the plurality of guide targets are taken into account is not limited to the above-described example.

The state control apparatus according to the present embodiment then causes an external display apparatus to execute the determined program (an example of the processing relating to the feeling guiding medium). The state control apparatus according to the present embodiment, for example, causes the display apparatus to execute the determined program by transmitting a command for executing the program and the determined program (or information indicating a location where the determined program is stored) to the display apparatus.

By the state control apparatus according to the present embodiment causing the display apparatus to execute the determined program, it is possible to change display on the display screen of the display apparatus. Therefore, by the state control apparatus according to the present embodiment causing the display apparatus to execute the determined program, for example, the state of the target feeling of the guide target is guided to the predetermined set state.

The apparatus at the guide target side senses the enzyme activity level S (S910).

The state control apparatus according to the present embodiment, for example, updates the program list data as in step S712 in FIG. 20 (S912).

The state control apparatus according to the present embodiment determines whether or not the enzyme activity level S is in a desired state as in S316 in FIG. 12 (S914).

In the case where it is not determined in step S914 that the enzyme activity level S is in the desired state, the state control apparatus according to the present embodiment determines whether or not it is a timing for switching as in S318 in FIG. 12 (S916).

In the case where it is not determined in step S916 that it is a timing for switching, the state control apparatus according to the present embodiment, for example, repeats the processing from step S914.

In the case where it is determined in step S916 that it is a timing for switching, the state control apparatus according to the present embodiment, for example, repeats the processing from step S908.

In the case where it is determined in step S914 that the enzyme activity level S is in the desired state, or in the case where it is not determined in step S906 that the enzyme activity level S is equal to or greater than the threshold $S_L$, the state control apparatus according to the present embodiment causes the apparatus at the guide target side to determine whether or not to finish the processing.

The apparatus at the guide target side determines whether or not to finish the processing as in S320 in FIG. 12 (S918).

In the case where it is not determined in step S918 to finish the processing, the apparatus at the guide target side, for example, repeats the processing from step S902. Further, in the case where it is determined in step S918 to finish the processing, the apparatus at the guide target side finishes the processing illustrated in FIG. 22.

The state control apparatus according to the present embodiment and the apparatus at the guide target side, for example, perform the processing illustrated in FIG. 22 as the processing according to the sixth application example of the state control method according to the present embodiment.

Note that the example of the processing according to the sixth application example of the state control method according to the present embodiment is not limited to the example illustrated in FIG. 22.

For example, the program determined by the state control apparatus according to the present embodiment in step S908 is not limited to the program relating to change of display and may be a program for further changing sound, odor, or the like.

[4-7] Seventh Application Example

As a fourth application example, an example of service which can be realized using the state control system (or the state control apparatus) according to the above-described first application example to sixth application example will be described.

Figure 23:
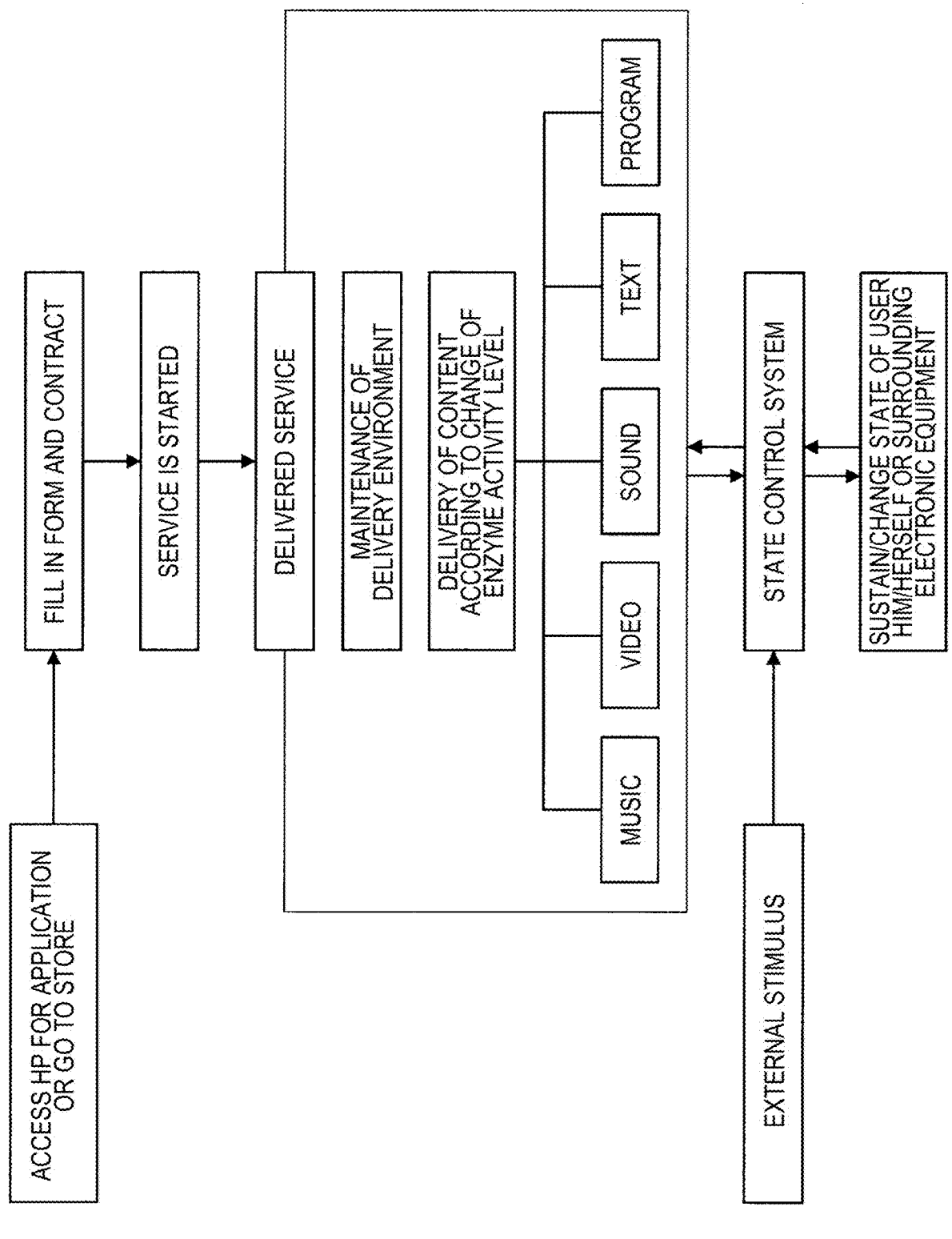
FIG. 23 is an explanatory diagram explaining an example of service which can be realized using a state control system according to the present embodiment (or a state control apparatus according to the present embodiment).

FIG. 23 is an explanatory diagram for explaining an example of service which can be realized using the state control system according to the present embodiment (or the state control apparatus according to the present embodiment). In the following description, a case will be described as an example where service is provided using the state control system according to the present embodiment.

For example, a person who desires delivery of service accesses a home page (HP) corresponding to the service or directly goes to a store corresponding to the service, and fills in forms, thereby, a contract is concluded, and service is started.

Examples of the delivered service (hereinafter, referred to as "delivered service") include, for example, maintenance of a delivery environment, and delivery of content data (such as, for example, music (song or sound), an image (a moving image or a still image), text (character string), data indicating sound and a program) according to change of the enzyme activity level S. The above-described program which can be included in the content data specifies operation of electronic equipment.

In the case where an external stimulus is given to a user (an example of the guide target) who receives delivered service, the state control system according to the present embodiment delivers the above-described content data relating to the delivered service to an apparatus of the user (for example, the apparatus at the guide target side), electronic equipment around the user (such as, for example, audio equipment, game equipment, a TV set, a display, a PC, a smartphone, a tablet type apparatus, an electronic book device, a clock, a lighting apparatus, an aroma generating apparatus, an air conditioner, a refrigerator, broadcasting equipment, attraction equipment, a vehicle, factory equipment, medical equipment and a robot) according to change of the enzyme activity level S. Through delivery of the above-described content data, it is possible to unconsciously maintain or change the state of the user or the electronic equipment.

[5] Effects Provided by Processing Relating to State Control Method According to Present Embodiment being Performed By the processing relating to the state control method according to the present embodiment being performed, for example, the effects as indicated in the following (A) to (D) are provided. Note that it goes without saying that the effects provided by the processing relating to the state control method according to the present embodiment being performed are not limited to the effects indicated in the following (A) to (D).

(A) Because time-series data of the past change of the biological information of the user is associated with the content data, it is possible to predict at which timing the content data should be reproduced more appropriately, so that it is possible to naturally and effectively guide the state of the target feeling of the user to the desired state (for example, this effect is provided in various fields including entertainment and healthcare).

(B) Because it is possible to reuse the content data which provides the effect to other persons who have preference similar to preference of the user as well as the user him/herself who is the guide target according to the setting of the search range, it is possible to realize change to the desired state more effectively. Further, in this event, because content data with which the user is not familiar can be also reproduced, it is possible to allow the user who is the guide target to experience unexpected discovery or have fun which cannot be experienced through simple mechanical control. As a result, it is possible to continue the effect without depending on a use frequency of the state control system according to the present embodiment (or the state control apparatus according to the present embodiment).

(C) Because it is possible to notify the third party other than the guide target of change of the state of the target feeling of the guide target, it is possible to share the feeling with the third party even in the case where the guide target has difficulty in conveying feeling by words or expression (for example, in the case where the guide target is a disabled person, a patient, a pet, or the like).

(D) By setting a program for controlling the security lock level of the apparatus (such as, for example, factory equipment, a vehicle and medical equipment) as the content data, it is possible to suppress erroneous operation of the apparatus caused by feeling of displeasure of the user who is the guide target.

State Control Apparatus, State Control System According to Present Embodiment An example of the configuration of the state control apparatus according to the present embodiment and an example of the configuration of the state control system according to the present embodiment which can perform the above-described processing relating to the state control method according to the present embodiment will be described next.

[I] State Control Apparatus According to Present Embodiment

An example of the configuration of the state control apparatus according to the present embodiment which can perform the processing relating to the state control method according to the present embodiment will be described first.

Figure 24:
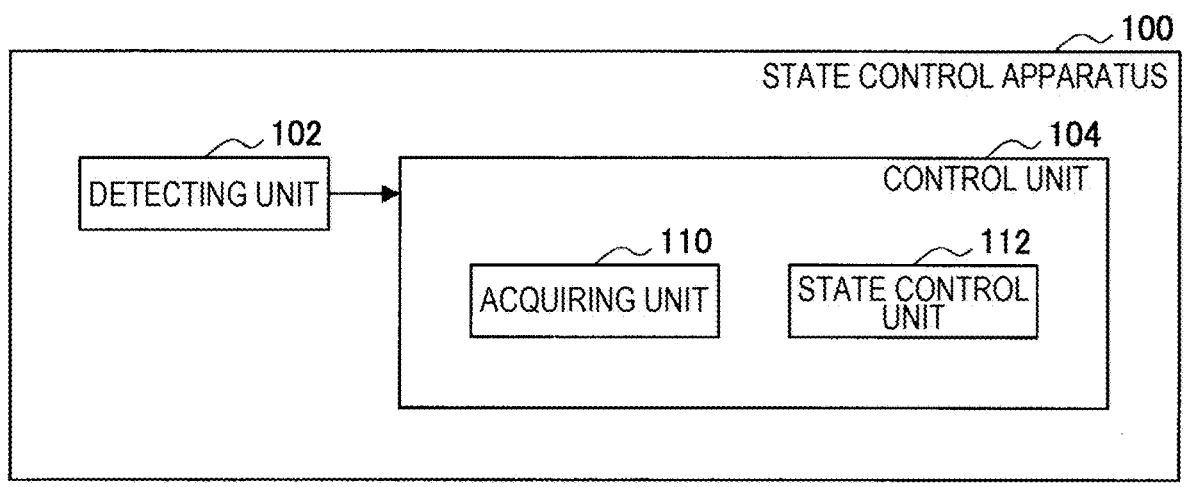
FIG. 24 is a block diagram illustrating an example of a configuration of the state control apparatus according to the present embodiment.

FIG. 24 is a block diagram illustrating an example of the configuration of the state control apparatus 100 according to the present embodiment. The state control apparatus 100 includes, for example, a detecting unit 102 and a control unit 104.

Further, the state control apparatus 100 may include, for example, a read only memory (ROM, not illustrated), a random access memory (RAM, not illustrated), a storage unit (not illustrated), a communication unit (not illustrated), an operating unit (not illustrated) which can be operated by the user, a display unit (not illustrated) which displays various screens on a display screen, or the like. The state control apparatus 100, for example, connects the above-described components using a bus which is used as a data transmission path.

The ROM (not illustrated) stores data for control such as a program or an operation parameter to be used by the control unit 104. The RAM (not illustrated) temporarily stores a program to be executed by the control unit 104.

The storage unit (not illustrated) is storage means of the state control apparatus 100, and, for example, stores various kinds of data such as data relating to the state control method according to the present embodiment, such as data indicating the content list and the content data, and application. Here, examples of the storage unit (not illustrated) include, for example, a magnetic recording medium such as a hard disk, a nonvolatile memory such as a flash memory, or the like. Further, the storage unit (not illustrated) may be detachable from the state control apparatus 100.

Examples of the communication unit include, for example, a communication interface which will be described later. Examples of the operating unit (not illustrated) include, for example, an operation input device which will be described later. Further, examples of the display unit (not illustrated) include, for example, a display device which will be described later.

Hardware Configuration Example of State Control Apparatus 100

Figure 25:
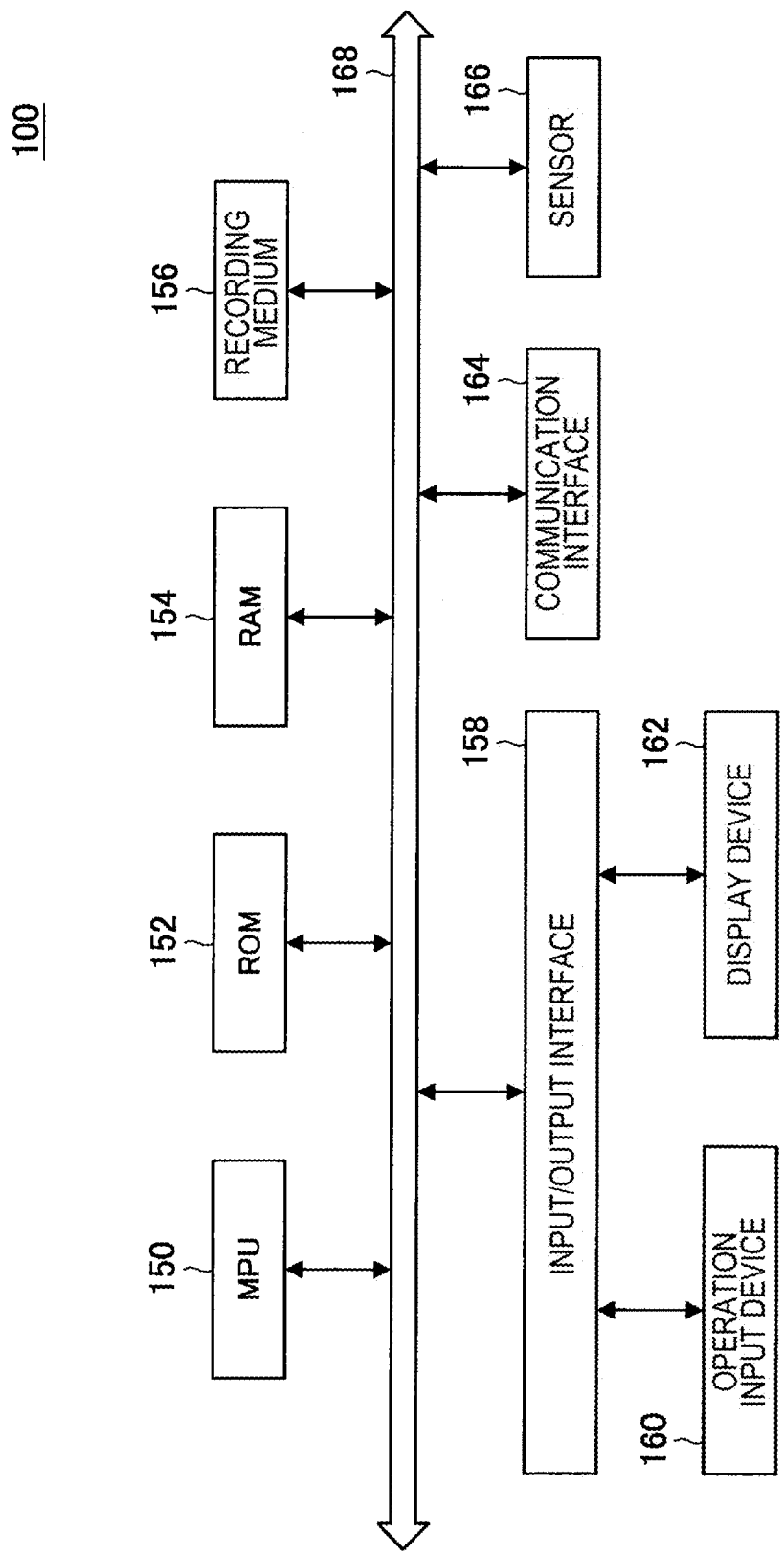
FIG. 25 is an explanatory diagram illustrating an example of a hardware configuration of the state control apparatus according to the present embodiment.

FIG. 25 is an explanatory diagram illustrating an example of a hardware configuration of the state control apparatus 100 according to the present embodiment. The state control apparatus 100 includes, for example, an MPU 150, a ROM 152, a RAM 154, a recording medium 156, an input/output interface 158, an operation input device 160, a display device 162, a communication interface 164 and a sensor 166. Further, the state control apparatus 100, for example, connects the components using a bus 168 which is used as a data transmission path.

The MPU 150 functions as one or more processors configured with an arithmetic circuit such as an MPU or the control unit 104 configured with various kinds of processing circuits and configured to control the whole of the state control apparatus 100. Further, the MPU 150 plays a role of, for example, an acquiring unit 110 which will be described later and a state control unit 112 in the state control apparatus 100.

The ROM 152 stores data for control such as a program or an operation parameter to be used by the MPU 150. The RAM 154, for example, temporarily stores a program to be executed by the MPU 150.

The recording medium 156 which functions as a storage unit (not illustrated), stores various kinds of data such as data relating to the state control method according to the present embodiment, such as data indicating the content list, and application. Here, examples of the recording medium 156 include, for example, a magnetic recording medium such as a hard disk and a nonvolatile memory such as a flash memory. Further, the recording medium 156 may be detachable from the state control apparatus 100.

The input/output interface 158, for example, connects the operation input device 160 and the display device 162. The operation input device 160 functions as an operating unit (not illustrated), and the display device 162 functions as a display unit (not illustrated). Here, examples of the input/output interface 158 include, for example, a universal serial bus (USB) terminal, a digital visual interface (DVI) terminal, a high-definition multimedia interface (HDMI) (registered trademark) terminal, various kinds of processing circuits, or the like.

Further, the operation input device 160 is, for example, provided on the state control apparatus 100 and connected to the input/output interface 158 inside the state control apparatus 100. Examples of the operation input device 160 include, for example, a button, a direction key, a rotary selector such as a jog dial and combination of these.

Further, the display device 162 is, for example, provided on the state control apparatus 100 and connected to the input/output interface 158 inside the state control apparatus 100. Examples of the display device 162 include, for example, a liquid crystal display, an organic electro-luminescence display (organic EL display, which is also referred to as an organic light emitting diode display (OLED display)), or the like.

Note that it goes without saying that the input/output interface 158 can be also connected to an external device such as an external operation input device (such as, for example, a keyboard and a mouse) and an external display device which are used as external apparatuses of the state control apparatus 100. Further, the display device 162 may be a device such as, for example, a touch panel, which can perform display and allow user operation.

The communication interface 164 which is communication means of the state control apparatus 100, functions as a communication unit (not illustrated) for performing communication with an external device such as an external display device or an external apparatus in a wired or wireless manner via a network (or directly). Here, examples of the communication interface 164 include, for example, a communication antenna and a radio frequency (RF) circuit (wireless communication), an IEEE 802.15.1 port and a transmission/reception circuit (wireless communication), an IEEE 802.11 port and a transmission/reception circuit (wireless communication), a local area network (LAN) terminal and a transmission/reception circuit (wired communication), or the like. Further, examples of the network according to the present embodiment include, for example, a wired network such as a LAN and a wide area network (WAN), the Internet using a communication protocol such as a transmission control protocol/internet protocol (TCP/IP), or the like.

The sensor 166 which is detecting means of the state control apparatus 100, plays a role of the detecting unit 102. Examples of the sensor 166 include, for example, an enzyme sensor. Further, the sensor 166 may further include other sensors such as a sensor for detecting a heart rate and a sensor for detecting an amount of perspiration in addition to the enzyme sensor.

The state control apparatus 100 performs the processing relating to the state control method according to the present embodiment, for example, with the configuration illustrated in FIG. 25. Note that the hardware configuration of the state control apparatus 100 according to the present embodiment is not limited to the configuration illustrated in FIG. 25.

For example, in the case where the state control apparatus 100 performs the processing using a detection result of an external detecting device having a function similar to that of the sensor 166, the state control apparatus 100 does not have to include the sensor 166.

Further, for example, in the case where communication is performed with external apparatuses via a connected external communication device, or in the case where processing is performed in a stand-alone manner, the state control apparatus 100 does not have to include the communication interface 164. Further, the state control apparatus 100 may include, for example, a plurality of communication interfaces complying with the same or different communication schemes.

Further, the state control apparatus 100 can, for example, employ a configuration which does not include the recording medium 156, the operation input device 160 and the display device 162.

Further, for example, the configuration illustrated in FIG. 25 (or the configuration according to a modified example) may be implemented with one or more integrated circuits (ICs).

Further, the state control apparatus 100 may be, for example, an intraoral device having a configuration described with reference to A in FIG. 11 to C in FIG. 11.

Referring to FIG. 24 again, an example of the configuration of the state control apparatus 100 will be described. The detecting unit 102 which is detecting means of the state control apparatus 100, for example, outputs a signal according to the detection result of a detection target (an example of the detection result). Examples of the detecting unit 102 include, for example, an enzyme sensor, or the like. Further, the detecting unit 102 may be configured with a plurality of sensors including an enzyme sensor and other sensors such as a sensor for detecting a heart rate and a sensor for detecting an amount of perspiration.

The control unit 104 which is, for example, configured with an MPU, plays a role of controlling the whole of the state control apparatus 100. Further, the control unit 104 includes, for example, an acquiring unit 110 and a state control unit 112, and plays a role of initiatively performing the processing relating to the state control method according to the present embodiment.

The acquiring unit 110 plays a role of initiatively performing the processing of the above-described (1) (acquisition processing) and acquires a state index. The acquiring unit 110 performs the acquisition processing according to the first example indicated in the above-described (1-1) and the acquisition processing according to the second example indicated in the above-described (1-2).

The state control unit 112 plays a role of initiatively performing the processing of the above-described (2) (state control processing). The state control unit 112 determines the feeling guiding medium to be used for guiding the state of the target feeling based on the state index acquired in the acquiring unit 110 and the pattern information associated with the feeling guiding medium. The state control unit 112 then controls the state of the target feeling of the guide target by performing processing relating to the determined feeling guiding medium.

More specifically, the state control unit 112 performs the state control processing according to the first example indicated in the above-described (2-1) to the seventh example indicated in the above-described (2-7).

Because the control unit 104 includes the acquiring unit 110 and the state control unit 112, the control unit 104, for example, initiatively performs the processing relating to the state control method according to the present embodiment.

The state control apparatus 100 performs the processing relating to the state control method according to the present embodiment (for example, the processing indicated in the above-described (1) (acquisition processing) and the processing indicated in the above-described (2) (state control processing)) with, for example, the configuration illustrated in FIG. 24.

Therefore, the state control apparatus 100 can guide the state of the feeling of the guide target to the predetermined set state with, for example, the configuration illustrated in FIG. 24.

Further, with, for example, the configuration illustrated in FIG. 24, the state control apparatus 100, for example, can provide effects as described above, provided by the processing relating to the state control method according to the present embodiment being performed.

Note that the configuration of the state control apparatus according to the present embodiment is not limited to the configuration illustrated in FIG. 24.

For example, the state control apparatus according to the present embodiment can include one or both of the acquiring unit 110 and the state control unit 112 illustrated in FIG. 24 separately from the control unit 104 (for example, using other processing circuits).

Further, as described above, the processing relating to the state control method according to the present embodiment is divided into the above-described acquisition processing and the above-described state control processing for convenience sake. Therefore, the configuration for implementing the processing relating to the state control method according to the present embodiment is not limited to the acquiring unit 110 and the state control unit 112 illustrated in FIG. 24 and can be a configuration according to how the processing relating to the state control method according to the present embodiment is divided.

Further, for example, in the case where processing is performed using a detection result of an external detecting device having a function and a configuration similar to those of the detecting unit 102, the state control apparatus according to the present embodiment does not have to include the detecting unit 102.

[II] State Control System According to Present Embodiment

An example of the configuration of the state control system according to the present embodiment which can perform the processing relating to the state control method according to the present embodiment will be described next.

Figure 26:
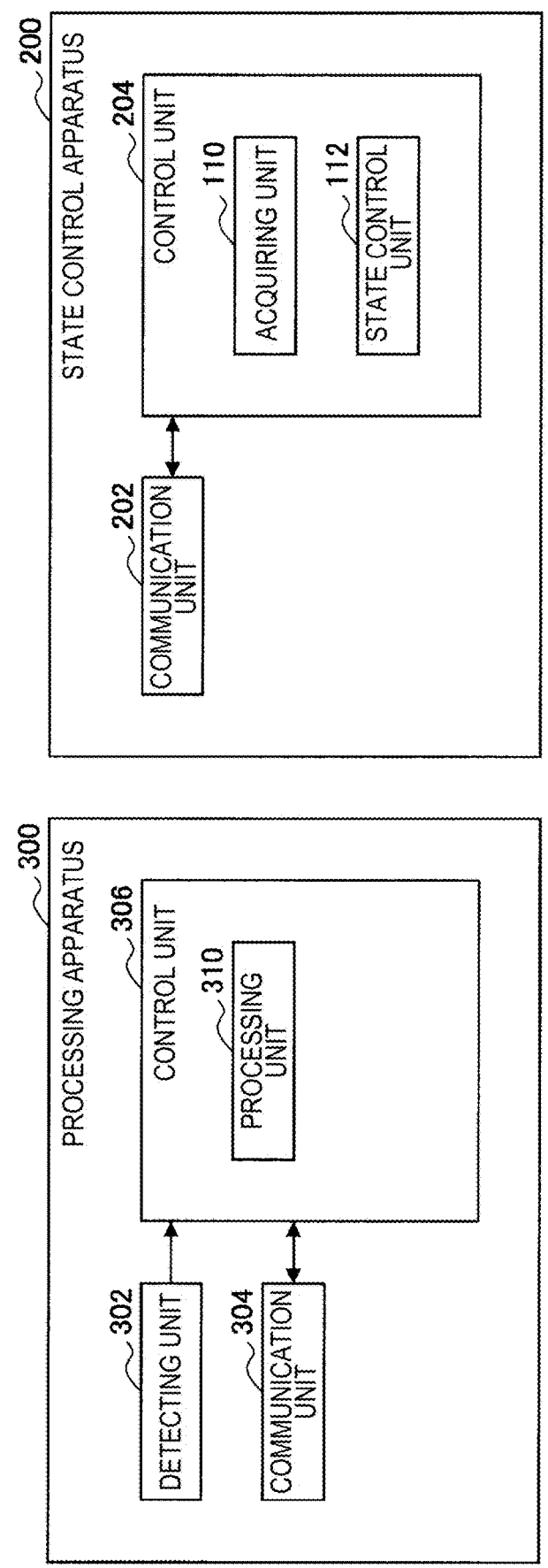
FIG. 26 is a block diagram illustrating an example of a configuration of the state control system according to the present embodiment.

FIG. 26 is a block diagram illustrating an example of the configuration of the state control system 1000 according to the present embodiment. The state control system 1000 includes a state control apparatus 200 and a processing apparatus 300. In the state control system 1000, the processing apparatus 300, for example, corresponds to the apparatus at the guide target side, which forms the state control system according to the above-described first application example to the above-described sixth application example.

The state control apparatus 200 causes the processing apparatus 300 to guide the state of the target feeling of the guide target to the predetermined set state by causing the processing apparatus 300 to perform the processing using the feeling guiding medium. Further, the processing circuit 300 performs the processing using the feeling guiding medium.

[II-1] State Control Apparatus 200

The state control apparatus 200 includes, for example, a communication unit 202 and a control unit 204.

Further, the state control apparatus 200 may include, for example, a ROM (not illustrated), a RAM (not illustrated), a storage unit (not illustrated), an operating unit (not illustrated), a display unit (not illustrated), or the like. The state control apparatus 200, for example, connects the above-described components using a bus which is used as a data transmission path.

Hardware Configuration Example of State Control Apparatus 200

The state control apparatus 200, for example, has a hardware configuration similar to that of the state control apparatus 100 illustrated in FIG. 25. Note that it goes without saying that the hardware configuration of the state control apparatus 200 is not limited to the configuration illustrated in FIG. 25.

The communication unit 202 which is communication means of the state control apparatus 200, performs communication with an external device such as an external display device and an external apparatus such as the processing apparatus 300 in a wired or wireless manner via a network (or directly). Further, communication of the communication unit 202 is controlled by, for example, the control unit 204.

Here, while examples of the communication unit 202 include, for example, a communication antenna, an RF circuit, a LAN terminal, a transmission/reception circuit, or the like, the configuration of the communication unit 202 is not limited to the above-described configuration. For example, the communication unit 202 may have a configuration which complies with arbitrary standards and which allows communication using a USB terminal and a transmission/reception circuit, an infrared communication port and a transmission/reception circuit, or the like, or an arbitrary configuration which allows communication with an external apparatus via a network. Further, the communication unit 202 may employ a configuration which allows communication with one or more external apparatuses using a plurality of communication schemes.

The control unit 204, which is configured with, for example, an MPU, or the like, plays a role of controlling the whole of the state control apparatus 200. Further, the control unit 204 includes, for example, an acquiring unit 110 and a state control unit 112, and initiatively performs processing relating to the state control method according to the present embodiment. As an example, the control unit 204 performs processing at the state control apparatus side in, for example, FIG. 12, FIG. 14, FIG. 15, FIG. 16, FIG. 20, FIG. 21 and FIG. 22.

The state control apparatus 200 performs the processing relating to the state control method according to the present embodiment (for example, the processing indicated in the above-described (1) (acquisition processing) and the processing indicated in the above-described (2) (state control processing)) with, for example, the configuration illustrated in FIG. 26.

Therefore, the state control apparatus 200 can guide the state of the feeling of the guide target to the predetermined set state with, for example, the configuration illustrated in FIG. 26.

Note that the configuration of the state control apparatus of the state control system according to the present embodiment is not limited to the configuration illustrated in FIG. 26.

For example, the state control apparatus according to the present embodiment does not have to include the communication unit 202 in the case where communication is performed with an external apparatus via an external communication device having a function and a configuration similar to those of the communication unit 202.

[II-2] Processing Apparatus 300

The processing apparatus 300 includes, for example, a detecting unit 302, a communication unit 304 and a control unit 306.

Hardware Configuration Example of Processing Apparatus 300

The processing apparatus 300 has, for example, the configuration described with reference to A in FIG. 11 to C in FIG. 11. Note that it goes without saying that the configuration of the processing apparatus 300 is not limited to the configuration described with reference to A in FIG. 11 to C in FIG. 11.

The detecting unit 302, which is detecting means of the processing apparatus 300, for example, outputs a signal according to a detection result of the detection target (an example of the detection result). The detecting unit 302, for example, has a function and a configuration similar to those of the detecting unit 102 illustrated in FIG. 24.

The communication unit 304, which is communication means of the processing apparatus 300, performs communication with an external apparatus such as the state control apparatus 200 in a wired or wireless manner via a network (or directly). Further, communication of the communication unit 304 is controlled by, for example, the control unit 306.

Here, the communication unit 304 is, for example, configured with a communication device complying with a communication scheme corresponding to the communication scheme of the communication unit 202 of the state control apparatus 200.

The control unit 306, which is configured with, for example, an MPU, or the like, plays a role of controlling the whole of the processing apparatus 300. Further, the control unit 306 includes, for example, the processing unit 310 and performs various kinds of processing such as processing using the feeling guiding medium. As an example, the processing unit 310 performs the processing of the apparatus at the guide target side in, for example, FIG. 12, FIG. 14, FIG. 15, FIG. 16, FIG. 20, FIG. 21 and FIG. 22.

The processing apparatus 300 performs various kinds of processing such as processing using the feeling guiding medium with, for example, the configuration illustrated in FIG. 26.

Note that the configuration of the processing apparatus of the state control system according to the present embodiment is not limited to the configuration illustrated in FIG. 26.

For example, in the case where an external detecting device having a function and a configuration similar to those of the detecting unit 302 is connected, the processing apparatus according to the present embodiment does not have to include the detecting unit 302.

Further, for example, in the case where communication is performed with an external apparatus via an external communication device having a function and a configuration similar to those of the communication unit 304, the state control apparatus according to the present embodiment does not have to include the communication unit 202.

The state control system 1000, for example, includes the state control apparatus 200 and the processing apparatus 300 in the configuration illustrated in FIG. 26.

Here, in the state control system 1000, the processing relating to the state control method according to the present embodiment (for example, the processing indicated in the above-described (1) (acquisition processing) and the processing indicated in the above-described (2) (state control processing)) is performed at the state control apparatus 200.

Therefore, by, for example, the state control apparatus 200 and the processing apparatus 300 in the configuration illustrated in FIG. 26 being provided, it is possible to realize a state control system which can guide the state of the feeling of the guide target to the predetermined set state.

Further, by, for example, the state control apparatus 200 and the processing apparatus 300 in the configuration illustrated in FIG. 26 being provided, in the state control system according to the present embodiment, for example, it is possible to provide an effect as described above, provided by the processing relating to the state control method according to the present embodiment being performed.

While the present embodiment has been described above using an example of the state control apparatus, the present embodiment is not limited to the above-described embodiment. The present embodiment can be applied to various equipment such as, for example, a computer such as a PC and a server, a communication apparatus such as a smartphone and a mobile phone, a tablet type apparatus, a video/music reproduction apparatus (or a video/music recording and reproducing apparatus), game equipment, a display apparatus and a TV set. Further, the present embodiment can be also applied to, for example, the intraoral device as illustrated in A in FIG. 11 to C in FIG. 11. Further, the present embodiment can be also applied to, for example, a processing IC which can be incorporated into equipment as described above.

Further, the state control apparatus according to the present embodiment may be applied to a system such as, for example, cloud computing, which includes one or more apparatuses assuming connection to a network (or communication among apparatuses). That is, the above-described state control apparatus according to the present embodiment can be implemented as, for example, a system configured with a plurality of apparatuses.

In the case where the above-described state control apparatus according to the present embodiment is implemented as a system such as, for example, cloud computing, the system according to the present embodiment controls the state of the target feeling of the guide target by performing, for example, the processing relating to the state control method according to the present embodiment and causing the processing apparatus which can perform communication in a wired or wireless manner to perform the processing using the feeling guiding medium.

Further, while the processing apparatus has been described as a component of the state control system according to the present embodiment, the present embodiment is not limited to this example. The present embodiment can be applied to various equipment such as an apparatus which can be used by being worn by the guide target, such as, for example, the intraoral device as illustrated in A in FIG. 11 to C in FIG. 11. Further, in the case where an external detecting device is connected to the processing apparatus according to the present embodiment, the processing apparatus does not have to be, for example, an apparatus which can be used by being worn by the guide target.

Program According to Present Embodiment

By a program for causing a computer to function as the state control apparatus according to the present embodiment (for example, a program which can execute the processing relating to the state control method according to the present embodiment, such as the processing indicated in the above-described (1) (acquisition processing) and the processing indicated in the above-described (2) (state control processing)) being executed by the processor, or the like, at the computer, it is possible to guide the state of feeling of the guide target to the predetermined set state.

Further, by a program for causing a computer to function as the state control apparatus according to the present embodiment being executed by the processor, or the like, at the computer, it is possible to provide effects provided by the above-described processing relating to the state control method according to the present embodiment being performed.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the above shows that a program (computer program) causing a computer to function as the state control apparatus according to the present embodiment is provided, but the present embodiment can further provide a recording medium caused to store the program.

The above configuration shows an example of the present embodiment and naturally comes under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)

A state control apparatus including:

an acquiring unit configured to acquire a state index indicating a state of target feeling based on biological information corresponding to the target feeling which is feeling of a target to be guided, the biological information being detected from a guide target whose state of feeling is to be guided; and a state control unit configured to determine a feeling guiding medium to be used for guiding the state of the target feeling based on the acquired state index and pattern information which is associated with the feeling guiding medium for guiding the state of the target feeling and which indicates a pattern of temporal change of the state index so that the state of the target feeling becomes a predetermined set state, and control the state of the target feeling of the guide target by performing processing relating to the determined feeling guiding medium, wherein the biological information includes information indicating a detection result of an enzyme.

(2)

The state control apparatus according to (1), wherein the state control unit determines the feeling guiding medium to be used for guiding the state of the target feeling of the guide target among feeling guiding media having patterns of change opposite to the pattern of temporal change of the acquired state index.

(3)

The state control apparatus according to (1) or (2), wherein, in the case where control by processing relating to the determined feeling guiding medium is started, the state control unit redetermines the feeling guiding medium based on time elapsed since the control by the processing relating to the determined feeling guiding medium is started and the pattern information associated with the determined feeling guiding medium so that the state of the target feeling becomes the predetermined state, and the state control unit switches the feeling guiding medium to be used for controlling the state of the target feeling of the guide target from the feeling guiding medium being used to the redetermined feeling guiding medium and controls the state of the target feeling of the guide target.

(4)

The state control apparatus according to (3), wherein the redetermined feeling guiding medium is the feeling guiding medium having a pattern of change opposite to the pattern of temporal change of the state index in the pattern information associated with the determined feeling guiding medium.

(5)

The state control apparatus according to any one of (1) to (4), wherein, in the case where the acquired state index is greater than a predetermined set threshold or in the case where the acquired state index becomes equal to or greater than the threshold, the state control unit starts control of the state of the target feeling of the guide target.

(6)

The state control apparatus according to any one of (1) to (5), wherein the state control unit determines the feeling guiding medium to be used for guiding the state of the target feeling of the guide target among feeling guiding media which satisfy set search conditions of the feeling guiding medium.

(7)

The state control apparatus according to (6), wherein the search conditions include conditions indicating a search range of the feeling guiding medium, and the state control unit determines the feeling guiding medium to be used for guiding the state of the target feeling of the guide target among feeling guiding media included in a search range indicated by the set search conditions.

(8)

The state control apparatus according to (7), wherein the state control unit performs first determination processing of determining the feeling guiding medium to be used for guiding the state of the target feeling of the guide target among feeling guiding media included in a first range out of the search range indicated by the set search conditions, and in the case where the feeling guiding medium to be used for guiding the state of the target feeling is not determined through the first determination processing, the state control unit performs second determination processing of determining the feeling guiding medium to be used for guiding the state of the target feeling of the guide target among feeling guiding media included in a second range other than the first range out of the search range indicated by the search conditions.

(9)

The state control apparatus according to (8), wherein, in the case where the feeling guiding medium to be used for guiding the state of the target feeling is not determined through the second determination processing, the state control unit changes the search range indicated by the search conditions, and the state control unit performs third determination processing of determining the feeling guiding medium to be used for guiding the state of the target feeling of the guide target among feeling guiding media included in the changed search range.

(10)

The state control apparatus according to any one of (1) to (9), wherein the state control unit gives notification of the state of the target feeling of the guide target.

(11)

The state control apparatus according to any one of (1) to (10), wherein the state index is an enzyme activity level.

(12)

The state control apparatus according to any one of (1) to (11),
wherein the biological information includes information indicating a detection result of an enzyme whose time constant of reaction to an external stimulus provided to the guide target is within a predetermined period or information indicating a detection result of an enzyme of which the time constant is shorter than the predetermined period.

(13)
The state control apparatus according to any one of (1) to (12),
wherein the enzyme is salivary amylase.

(14)
The state control apparatus according to any one of (1) to (13),
wherein the acquiring unit acquires the state index by calculating the state index based on the biological information according to a detection result of a detecting device.

(15)
The state control apparatus according to (14), further including:
a detecting unit having the detecting device,
wherein the acquiring unit calculates the state index based on the biological information according to a detection result at the detecting unit.

(16)
The state control apparatus according to any one of (1) to (13),
wherein the acquiring unit acquires the state index from an external apparatus through communication with the external apparatus.

(17)
The state control apparatus according to any one of (1) to (16),
wherein the state control unit updates the pattern information associated with the determined feeling guiding medium based on the acquired state index.

(18)
The state control apparatus according to any one of (1) to (17),
wherein the state control apparatus is an intraoral device.

(19)
A state control method executed by a state control apparatus, the state control method including:
a step of acquiring a state index indicating a state of target feeling based on biological information corresponding to the target feeling which is feeling of a target to be guided, the biological information being detected from a guide target whose state of feeling is to be guided; and
a step of determining a feeling guiding medium to be used for guiding the state of the target feeling based on the acquired state index and pattern information which is associated with the feeling guiding medium for guiding the state of the target feeling and which indicates a pattern of temporal change of the state index so that the state of the target feeling becomes a predetermined set state, and controlling the state of the target feeling of the guide target by performing processing relating to the determined feeling guiding medium,
wherein the biological information includes information indicating a detection result of an enzyme.

(20)
A state control system including:
a processing apparatus configured to perform processing using a feeling guiding medium for guiding a state of target feeling which is feeling of a target to be guided of a guide target whose state of feeling is to be guided; and
a state control apparatus configured to guide the state of the target feeling of the guide target to a predetermined set state by causing the processing apparatus to perform the processing using the feeling guiding medium,
wherein the state control apparatus includes
an acquiring unit configured to acquire a state index indicating the state of the target feeling based on biological information corresponding to the target feeling, the biological information being detected from the guide target, and
a state control unit configured to determine the feeling guiding medium to be used for guiding the state of the target feeling based on the acquired state index and pattern information which is associated with the feeling guiding medium and which indicates a pattern of temporal change of the state index so that the state of the target feeling becomes a predetermined set state, and control the state of the target feeling of the guide target by performing processing relating to the determined feeling guiding medium, and
the biological information includes information indicating a detection result of an enzyme.

REFERENCE SIGNS LIST 100, 200 state control apparatus
102, 302 detecting unit
104, 204, 306 control unit
110 acquiring unit
112 state control unit
202, 304 communication unit
300 processing apparatus
310 processing unit

The invention claimed is:
1. A state control apparatus comprising:
processing circuitry configured to:
acquire a state index indicating a state of target feeling based on biological information corresponding to the target feeling which is a feeling of a target to be guided, the biological information being detected from a guide target whose state of feeling is to be guided;
determine a feeling guiding medium to be used for guiding the state of the target feeling based on the acquired state index and pattern information which is associated with the feeling guiding medium for guiding the state of the target feeling and which indicates a pattern of temporal change of the state index so that the state of the target feeling becomes a predetermined set state;
control the state of the target feeling of the guide target by performing processing relating to the determined feeling guiding medium;
determine the feeling guiding medium to be used for guiding the state of the target feeling of the guide target among feeling guiding media which satisfy set search conditions of the feeling guiding medium, wherein the search conditions include conditions indicating a search range of the feeling guiding medium;
determine the feeling guiding medium to be used for guiding the state of the target feeling of the guide target among feeling guiding media included in a search range indicated by the set search conditions;
perform first determination processing of determining the feeling guiding medium to be used for guiding the state of the target feeling of the guide target among feeling guiding media included in a first range out of the search range indicated by the set search conditions; and in the case where the feeling guiding medium to be used for guiding the state of the target feeling is not determined through the first determination processing, perform second determination processing of determining the feeling guiding medium to be used for guiding the state of the target feeling of the guide target among feeling guiding media included in a second range other than the first range out of the search range indicated by the search conditions, wherein the biological information includes information indicating a detection result of an enzyme.

2. The state control apparatus according to claim 1, wherein the processing circuitry is configured to determine the feeling guiding medium to be used for guiding the state of the target feeling of the guide target among feeling guiding media having patterns of change opposite to the pattern of temporal change of the acquired state index.

3. The state control apparatus according to claim 1, wherein, in the case where control by processing relating to the determined feeling guiding medium is started, the processing circuitry is configured to predetermine the feeling guiding medium based on time elapsed since the control by the processing relating to the determined feeling guiding medium is started and the pattern information associated with the determined feeling guiding medium so that the state of the target feeling becomes the predetermined state, and to switch the feeling guiding medium to be used for controlling the state of the target feeling of the guide target from the feeling guiding medium being used to the redetermined feeling guiding medium and controls the state of the target feeling of the guide target.

4. The state control apparatus according to claim 3, wherein the redetermined feeling guiding medium is the feeling guiding medium having a pattern of change opposite to the pattern of temporal change of the state index in the pattern information associated with the determined feeling guiding medium.

5. The state control apparatus according to claim 1, wherein, in the case where the acquired state index is greater than a predetermined set threshold or in the case where the acquired state index becomes equal to or greater than the threshold, the processing circuitry is configured to start control of the state of the target feeling of the guide target.

6. The state control apparatus according to claim 1, wherein, in the case where the feeling guiding medium to be used for guiding the state of the target feeling is not determined through the second determination processing, the processing circuitry is configured to change the search range indicated by the search conditions, and to perform third determination processing of determining the feeling guiding medium to be used for guiding the state of the target feeling of the guide target among feeling guiding media included in the changed search range.

7. The state control apparatus according to claim 1, wherein the processing circuitry is configured to give notification of the state of the target feeling of the guide target.

8. The state control apparatus according to claim 1, wherein the state index is an enzyme activity level.

9. The state control apparatus according to claim 1, wherein the biological information includes information indicating the detection result of an enzyme whose time constant of reaction to an external stimulus provided to the guide target is within a predetermined period or information indicating a detection result of an enzyme of which the time constant is shorter than the predetermined period.

10. The state control apparatus according to claim 1, wherein the enzyme is salivary amylase.

11. The state control apparatus according to claim 1, wherein the processing circuitry is configured to acquire the state index by calculating the state index based on the biological information according to a detection result of a detecting device.

12. The state control apparatus according to claim 11, further comprising:
a detecting unit having the detecting device,
wherein the processing circuitry is configured to calculate the state index based on the biological information according to a detection result at the detecting unit.

13. The state control apparatus according to claim 1, wherein the processing circuitry is configured to acquire the state index from an external apparatus through communication with the external apparatus.

14. The state control apparatus according to claim 1, wherein the processing circuitry is configured to update the pattern information associated with the determined feeling guiding medium based on the acquired state index.

15. The state control apparatus according to claim 1, wherein the state control apparatus is an intraoral device.

16. A state control method executed by a state control apparatus, the state control method comprising:
acquiring, by processing circuitry, a state index indicating a state of target feeling based on biological information corresponding to the target feeling which is a feeling of a target to be guided, the biological information being detected from a guide target whose state of feeling is to be guided;
determining, by the processing circuitry, a feeling guiding medium to be used for guiding the state of the target feeling based on the acquired state index and pattern information which is associated with the feeling guiding medium for guiding the state of the target feeling and which indicates a pattern of temporal change of the state index so that the state of the target feeling becomes a predetermined set state;
controlling, by the processing circuitry, the state of the target feeling of the guide target by performing processing relating to the determined feeling guiding medium;
determining the feeling guiding medium to be used for guiding the state of the target feeling of the guide target among feeling guiding media which satisfy set search conditions of the feeling guiding medium, wherein the search conditions include conditions indicating a search range of the feeling guiding medium;
determining the feeling guiding medium to be used for guiding the state of the target feeling of the guide target among feeling guiding media included in a search range indicated by the set search conditions;
performing first determination processing of determining the feeling guiding medium to be used for guiding the state of the target feeling of the guide target among feeling guiding media included in a first range out of the search range indicated by the set search conditions; and
in the case where the feeling guiding medium to be used for guiding the state of the target feeling is not determined through the first determination processing, performing second determination processing of determining the feeling guiding medium to be used for guiding the state of the target feeling of the guide target among feeling guiding media included in a second range other than the first range out of the search range indicated by the search conditions, wherein the biological information includes information indicating a detection result of an enzyme.

17. A state control system comprising:

first processing circuitry configured to perform processing using a feeling guiding medium for guiding a state of target feeling which is a feeling of a target to be guided of a guide target whose state of feeling is to be guided; and a state control apparatus configured to guide the state of the target feeling of the guide target to a predetermined set state by causing the processing apparatus to perform the processing using the feeling guiding medium, wherein the state control apparatus includes
second processing circuitry configured to:
acquire a state index indicating the state of the target feeling based on biological information corresponding to the target feeling, the biological information being detected from the guide target;
determine the feeling guiding medium to be used for guiding the state of the target feeling based on the acquired state index and pattern information which is associated with the feeling guiding medium and which indicates a pattern of temporal change of the state index so that the state of the target feeling becomes a predetermined set state;
control the state of the target feeling of the guide target by performing processing relating to the determined feeling guiding medium;
determine the feeling guiding medium to be used for guiding the state of the target feeling of the guide target among feeling guiding media which satisfy set search conditions of the feeling guiding medium, wherein the search conditions include conditions indicating a search range of the feeling guiding medium;
determine the feeling guiding medium to be used for guiding the state of the target feeling of the guide target among feeling guiding media included in a search range indicated by the set search conditions;
perform first determination processing of determining the feeling guiding medium to be used for guiding the state of the target feeling of the guide target among feeling guiding media included in a first range out of the search range indicated by the set search conditions; and
in the case where the feeling guiding medium to be used for guiding the state of the target feeling is not determined through the first determination processing, perform second determination processing of determining the feeling guiding medium to be used for guiding the state of the target feeling of the guide target among feeling guiding media included in a second range other than the first range out of the search range indicated by the search conditions, and wherein the biological information includes information indicating a detection result of an enzyme.

* * * * *